United States Patent
Carceller González et al.

(10) Patent No.: US 8,431,580 B2
(45) Date of Patent: Apr. 30, 2013

(54) 4-AMINOPYRIMIDINE DERIVATIVES AS HISTAMINE $H_4$ RECEPTOR ANTAGONISTS

(75) Inventors: Elena Carceller González, Barcelona (ES); Eva Maria Medina Fuentes, Barcelona (ES); Robert Soliva Soliva, Barcelona (ES); Marina Virgili Bernadó, Barcelona (ES); Josep Martí Via, Barcelona (ES)

(73) Assignee: Palau Pharma, S.A., Barcelona (ES)

( * ) Notice: Subject to any disclaimer, the term of this patent is extended or adjusted under 35 U.S.C. 154(b) by 128 days.

(21) Appl. No.: 12/809,371

(22) PCT Filed: Dec. 18, 2008

(86) PCT No.: PCT/EP2008/067950
§ 371 (c)(1),
(2), (4) Date: Oct. 5, 2010

(87) PCT Pub. No.: WO2009/080721
PCT Pub. Date: Jul. 2, 2009

(65) Prior Publication Data
US 2011/0039817 A1 Feb. 17, 2011

Related U.S. Application Data

(60) Provisional application No. 61/031,534, filed on Feb. 26, 2008.

(30) Foreign Application Priority Data

Dec. 21, 2007 (EP) .................................. 07382006

(51) Int. Cl.
*A01N 43/54* (2006.01)
(52) U.S. Cl.
USPC ............ 514/256; 544/326; 548/518; 548/950

(58) Field of Classification Search .................. 514/256; 544/326; 548/518, 950
See application file for complete search history.

(56) References Cited

FOREIGN PATENT DOCUMENTS
EP       1 505 064 A     2/2005
WO       WO 2005/054239 A   6/2005

OTHER PUBLICATIONS

Jordan, V. C. Nature Reviews: Drug Discovery, 2, 2003, 205.*
Hackam, et al. JAMA, 296(14), 2006, 1731-1732.*
Altenbach, et al. Journal of Medicinal Chemistry, 51(20), 2008, 6571-6580.*
International Search Report for International Application No. PCT/EP2008/067950 mailed Jul. 7, 2009.
Zhang M et al: "The histamine H4 receptor in autoimmune disease" Expert Opinion on Investigational Drugs, Ashley Publications Ltd., London, GB, vol. 15, No. 11, Jan. 1, 2006, pp. 1443-1452, XP008086654; ISSN: 1354-3784.

* cited by examiner

*Primary Examiner* — Douglas M Willis
(74) *Attorney, Agent, or Firm* — Finnegan, Henderson, Farabow, Garrett & Dunner, L.L.P.

(57) ABSTRACT

4-Aminopyrimidine derivatives of formula (I) that are useful as histamine H4 receptor antagonists.

(I)

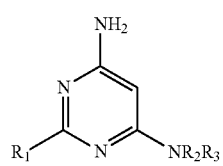

37 Claims, No Drawings ously
4-AMINOPYRIMIDINE DERIVATIVES AS HISTAMINE H₄ RECEPTOR ANTAGONISTS

CROSS-REFERENCE TO RELATED APPLICATIONS

This application is a National Stage Application of PCT/EP2008/067950, filed Dec. 18, 2008, and claims priority to U.S. Provisional Application No. 61/031,534, filed Feb. 26, 2008 and European Application EP 07382006.0, filed Dec. 21, 2007, all of which are incorporated herein by reference.

TECHNICAL FIELD OF THE INVENTION

The present invention relates to a new series of 4-aminopyrimidine derivatives, procedures to prepare them, pharmaceutical compositions comprising these compounds as well as their use in therapy.

BACKGROUND OF THE INVENTION

Histamine is one of the most potent mediators of immediate hypersensitivity reactions. While the effects of histamine on smooth muscle cell contraction, vascular permeability and gastric acid secretion are well known, its effects on the immune system are only now beginning to become unveiled.

A few years ago, a novel histamine receptor, which was named $H_4$, was cloned by several research groups working independently (Oda T et al, *J Biol Chem* 2000, 275: 36781-6; Nguyen T et al, *Mol Pharmacol* 2001, 59: 427-33). As the other members of its family, it is a G-protein coupled receptor (GPCR) containing 7 transmembrane segments. However, the $H_4$ receptor has low homology with the three other histamine receptors (Oda T et al); it is remarkable that it shares only a 35% homology with the $H_3$ receptor. While the expression of the $H_3$ receptor is restricted to cells of the central nervous system, the expression of the $H_4$ receptor has been mainly observed in cells of the haematopoietic lineage, in particular eosinophils, mast cells, basophils, dendritic cells and T-cells (Oda T et al). The fact that the $H_4$ receptor is highly distributed in cells of the immune system suggests the involvement of this receptor in immuno-inflammatory responses. Moreover, this hypothesis is reinforced by the fact that its gene expression can be regulated by inflammatory stimuli such as interferon, TNFα and IL-6. Nevertheless, the $H_4$ receptor is also expressed in other types of cells such as human synovial cells obtained from patients suffering from rheumatoid arthritis (Wojtecka-Lukasik E et al, *Ann Rheum Dis* 2006, 65 (Suppl II): 129; Ikawa Y et al, *Biol Pharm Bull* 2005, 28: 2016-8) and osteoarthritis (Grzybowska-Kowalczyk A et al, European Histamine Research Society XXXVI Annual Meeting, Florence, Italy, 2007, P-11), and in the human intestinal tract (Sander L E et al, *Gut* 2006, 55: 498-504). An increase in the expression of the $H_4$ receptor has also been reported in nasal polyp tissue in comparison to nasal mucosa of healthy people (Jókúti A et al, *Cell Biol Int* 2007, 31: 1367-70).

Recent studies with specific ligands of the $H_4$ receptor have helped to delimit the pharmacological properties of this receptor. These studies have evidenced that several histamine-induced responses in eosinophils such as chemotaxis, conformational change and CD11b and CD54 up-regulation are specifically mediated by the $H_4$ receptor (Ling P et al, *Br J Pharmacol* 2004, 142:161-71; Buckland K F et al, *Br J Pharmacol* 2003, 140:1117-27). In dendritic cells, the $H_4$ receptor has been shown to affect maturation, cytokine production and migration of these cells (Jelinek I et al, 1ˢᵗ Joint Meeting of European National Societies of Immunology, Paris, France, 2006, PA-1255). Moreover, the role of the $H_4$ receptor in mast cells has been studied. Although $H_4$ receptor activation does not induce mast cell degranulation, histamine and other proinflammatory mediators are released; moreover, the $H_4$ receptor has been shown to mediate chemotaxis and calcium mobilization of mast cells (Hofstra C L et al, *J Pharmacol Exp Ther* 2003, 305: 1212-21). With regard to T-lymphocytes, it has been shown that $H_4$ receptor activation induces T-cell migration and preferentially attracts a T-lymphocyte population with suppressor/regulatory phenotype and function (Morgan R K et al, American Thoracic Society Conference, San Diego, USA, 2006, P-536), as well as regulating the activation of CD4+ T cells (Dunford P J et al, *J Immunol* 2006, 176: 7062-70). As for the intestine, the distribution of the $H_4$ receptor suggests that it may have a role in the control of peristalsis and gastric acid secretion (Morini G et al, European Histamine Research Society XXXVI Annual Meeting, Florence, Italy, 2007, OR-10).

The various functions of the $H_4$ receptor observed in eosinophils, mast cells and T-cells suggest that this receptor can play an important role in the immuno-inflammatory response. In fact, $H_4$ receptor antagonists have shown in vivo activity in murine models of peritonitis (Thurmond R L et al, *J Pharmacol Exp Ther* 2004, 309: 404-13), pleurisy (Takeshita K et al, *J Pharmacol Exp Ther* 2003, 307: 1072-8) and scratching (Bell J K et al, *Br J Pharmacol* 2004,142:374-80). In addition, $H_4$ receptor antagonists have demonstrated in vivo activity in experimental models of allergic asthma (Dunford P J et al, 2006), inflammatory bowel disease (Varga C et al, *Eur J Pharmacol* 2005, 522:130-8), pruritus (Dunford P J et al, *J Allergy Clin Immunol* 2007, 119: 176-83), atopic dermatitis (Cowden J M et al, *J Allergy Clin Immunol* 2007; 119 (1): S239 (Abs 935), American Academy of Allergy, Asthma and Immunology 2007 AAAAI Annual Meeting, San Diego, USA), ocular inflammation (Zampeli E et al, European Histamine Research Society XXXVI Annual Meeting, Florence, Italy, 2007, OR-36), edema and hyperalgesia (Coruzzi G et al, *Eur J Pharmacol* 2007, 563: 240-4), and neuropathic pain (Cowart M D et al., *J Med. Chem.* 2008; 51 (20): 6547-57).

It is therefore expected that $H_4$ receptor antagonists can be useful for the treatment of allergic, immunological and inflammatory diseases, and pain.

Accordingly, it would be desirable to provide novel compounds having $H_4$ receptor antagonist activity and which are good drug candidates. In particular, preferred compounds should bind potently to the histamine $H_4$ receptor whilst showing little affinity for other receptors. In addition to binding to $H_4$ receptors, compounds should further exhibit good pharmacological activity in in vivo disease models Moreover, compounds should reach the target tissue or organ when administered via the chosen route of administration and possess favourable pharmacokinetic properties. In addition, they should be non-toxic and demonstrate few side-effects.

DESCRIPTION OF THE INVENTION

One aspect of the present invention relates to compounds of formula I

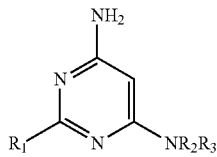

wherein:
$R_1$ represents:
(1) $C_{1-8}$ alkyl;
(2) $C_{3-8}$ cycloalkyl-$C_{0-6}$ alkyl;
(3) aryl-$C_{1-6}$ alkyl;
wherein in groups (1) to (3) any alkyl group may be optionally substituted with one or more halogen groups and the $C_{3-8}$ cycloalkyl group may be optionally substituted with one or more substituents independently selected from $C_{1-4}$ alkyl, halogen and aryl;
(4) a group of formula (i)

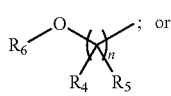

(5) a group of formula (ii):

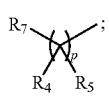

$R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group;
or $R_2$ represents H or $C_{1-4}$ alkyl, and $R_3$ represents azetidinyl, pyrrolidinyl, piperidinyl or azepanyl, which may be optionally substituted with one or more $C_{1-4}$ alkyl groups;
$R_a$ represents H or $C_{1-4}$ alkyl;
$R_b$ represents H or $C_{1-4}$ alkyl;
or $R_a$ and $R_b$ form, together with the N atom to which they are bound, an azetidinyl, pyrrolidinyl, piperidinyl or azepanyl group that may be optionally substituted with one or more $C_{1-4}$ alkyl groups;
$R_4$ and $R_5$ are independently selected from H and $C_{1-4}$ alkyl, and additionally one of the $R_4$ or $R_5$ groups may represent aryl or $C_{3-8}$ cycloalkyl-$C_{0-6}$ alkyl, and additionally two $R_4$ and $R_5$ groups on a same C atom may be bound together forming with said C atom a $C_{3-8}$ cycloalkyl group;
$R_6$ represents a group selected from $C_{1-8}$ alkyl, $C_{3-8}$ cycloalkyl-$C_{0-6}$ alkyl and aryl-$C_{0-4}$ alkyl, wherein any alkyl group may be optionally substituted with one or more halogen groups and the $C_{3-8}$ cycloalkyl group may be optionally substituted with one or more substituents independently selected from $C_{1-4}$ alkyl, halogen and aryl;
$R_7$ represents a saturated monocyclic 4- to 7-membered heterocyclic ring containing one O atom and not containing any other additional heteroatoms, wherein said ring may be bound to the rest of the molecule through any available C atom, and wherein $R_7$ may be optionally substituted with one or more groups independently selected from $C_{1-4}$ alkyl and halogen;
n represents 1, 2 or 3;
p represents 0, 1 or 2; and
aryl represents a phenyl group optionally substituted with one or more groups independently selected from $C_{1-4}$ alkyl, halogen, $C_{1-4}$ alkoxy, $C_{1-4}$ haloalkyl, $C_{1-4}$ haloalkoxy, cyano and amino.

The present invention also relates to the salts and solvates of the compounds of formula I.

Some compounds of formula I may have chiral centres that can give rise to various stereoisomers. The present invention relates to each of these stereoisomers and also to mixtures thereof.

The compounds of formula I show high affinity for the $H_4$ histamine receptor. Thus, another aspect of the invention relates to a compound of formula I

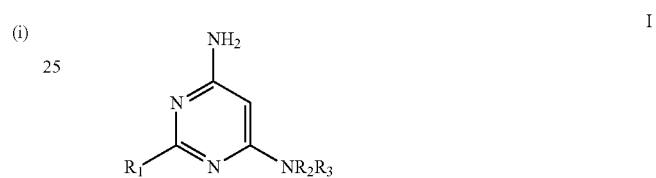

$R_1$ represents:
(1) $C_{1-8}$ alkyl;
(2) $C_{3-8}$ cycloalkyl-$C_{0-6}$ alkyl;
(3) aryl-$C_{1-6}$ alkyl;
wherein in groups (1) to (3) any alkyl group may be optionally substituted with one or more halogen groups and the $C_{3-8}$ cycloalkyl group may be optionally substituted with one or more substituents independently selected from $C_{1-4}$ alkyl, halogen and aryl;
(4) a group of formula (i)

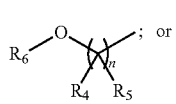

(5) a group of formula (ii):

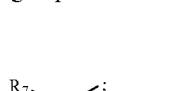

$R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group;

or $R_2$ represents H or $C_{1-4}$ alkyl, and $R_3$ represents azetidinyl, pyrrolidinyl, piperidinyl or azepanyl, which may be optionally substituted with one or more $C_{1-4}$ alkyl groups;

$R_a$ represents H or $C_{1-4}$ alkyl;

$R_b$ represents H or $C_{1-4}$ alkyl;

or $R_a$ and $R_b$ form, together with the N atom to which they are bound, an azetidinyl, pyrrolidinyl, piperidinyl or azepanyl group that may be optionally substituted with one or more $C_{1-4}$ alkyl groups;

$R_4$ and $R_5$ are independently selected from H and $C_{1-4}$ alkyl, and additionally one of the $R_4$ or $R_5$ groups may represent aryl or $C_{3-8}$ cycloalkyl-$C_{0-6}$ alkyl, and additionally two $R_4$ and $R_5$ groups on a same C atom may be bound together forming with said C atom a $C_{3-8}$ cycloalkyl group;

$R_6$ represents a group selected from $C_{1-8}$ alkyl, $C_{3-8}$ cycloalkyl-$C_{0-6}$ alkyl and aryl-$C_{0-4}$ alkyl, wherein any alkyl group may be optionally substituted with one or more halogen groups and the $C_{3-8}$ cycloalkyl group may be optionally substituted with one or more substituents independently selected from $C_{1-4}$ alkyl, halogen and aryl;

$R_7$ represents a saturated monocyclic 4- to 7-membered heterocyclic ring containing one O atom and not containing any other additional heteroatoms, wherein said ring may be bound to the rest of the molecule through any available C atom, and wherein $R_7$ may be optionally substituted with one or more groups independently selected from $C_{1-4}$ alkyl and halogen;

n represents 1, 2 or 3;

p represents 0, 1 or 2; and aryl represents a phenyl group optionally substituted with one or more groups independently selected from $C_{1-4}$ alkyl, halogen, $C_{1-4}$ alkoxy, $C_{1-4}$ haloalkyl, $C_{1-4}$ haloalkoxy, cyano and amino; for use in therapy.

Another aspect of the invention relates to a pharmaceutical composition which comprises a compound of formula I or a pharmaceutically acceptable salt thereof and one or more pharmaceutically acceptable excipients.

Another aspect of the present invention relates to the use of a compound of formula I or a pharmaceutically acceptable salt thereof for the manufacture of a medicament for the treatment of a disease mediated by the $H_4$ histamine receptor.

Another aspect of the present invention relates to the use of a compound of formula I or a pharmaceutically acceptable salt thereof for the manufacture of a medicament for the treatment of an allergic, immunological or inflammatory disease or pain.

Another aspect of the present invention relates to the use of a compound of formula I or a pharmaceutically acceptable salt thereof for the manufacture of a medicament for the treatment of an allergic, immunological or inflammatory disease. More preferably, the allergic, immunological or inflammatory disease is selected from respiratory diseases, ocular diseases, skin diseases, inflammatory bowel diseases, rheumatoid arthritis, multiple sclerosis, cutaneous lupus, systemic lupus erythematosus and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, dermatitis (e.g. atopic dermatitis), psoriasis, urticaria, pruritus, ulcerative colitis, Crohn's disease, rheumatoid arthritis, multiple sclerosis, cutaneous lupus, systemic lupus erythematosus and transplant rejection.

Another aspect of the present invention relates to the use of a compound of formula I or a pharmaceutically acceptable salt thereof for the manufacture of a medicament for the treatment of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a compound of formula I or a pharmaceutically acceptable salt thereof for use in the treatment of a disease mediated by the $H_4$ histamine receptor.

Another aspect of the present invention relates to a compound of formula I or a pharmaceutically acceptable salt thereof for use in the treatment of an allergic, immunological or inflammatory disease or pain.

Another aspect of the present invention relates to a compound of formula I or a pharmaceutically acceptable salt thereof for use in the treatment of an allergic, immunological or inflammatory disease. More preferably, the allergic, immunological or inflammatory disease is selected from respiratory diseases, ocular diseases, skin diseases, inflammatory bowel diseases, rheumatoid arthritis, multiple sclerosis, cutaneous lupus, systemic lupus erythematosus and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, dermatitis (e.g. atopic dermatitis), psoriasis, urticaria, pruritus, ulcerative colitis, Crohn's disease, rheumatoid arthritis, multiple sclerosis, cutaneous lupus, systemic lupus erythematosus and transplant rejection.

Another aspect of the present invention relates to a compound of formula I or a pharmaceutically acceptable salt thereof for use in the treatment of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to the use of a compound of formula I or a pharmaceutically acceptable salt thereof for the treatment of a disease mediated by the histamine $H_4$ receptor.

Another aspect of the present invention relates to the use of a compound of formula I or a pharmaceutically acceptable salt thereof for the treatment of an allergic, immunological or inflammatory disease or pain.

Another aspect of the present invention relates to the use of a compound of formula I or a pharmaceutically acceptable salt thereof for the treatment of an allergic, immunological or inflammatory disease. More preferably, the allergic, immunological or inflammatory disease is selected from respiratory diseases, ocular diseases, skin diseases, inflammatory bowel diseases, rheumatoid arthritis, multiple sclerosis, cutaneous lupus, systemic lupus erythematosus and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, dermatitis (e.g. atopic dermatitis), psoriasis, urticaria, pruritus, ulcerative colitis, Crohn's disease, rheumatoid arthritis, multiple sclerosis, cutaneous lupus, systemic lupus erythematosus and transplant rejection.

Another aspect of the present invention relates to the use of a compound of formula I or a pharmaceutically acceptable salt thereof for the treatment of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a method of treating a disease mediated by the histamine $H_4$ receptor in a subject in need thereof, specially a human being, which comprises administering to said subject a compound of formula I or a pharmaceutically acceptable salt thereof.

Another aspect of the present invention relates to a method of treating an allergic, immunological or inflammatory disease or pain in a subject in need thereof, specially a human being, which comprises administering to said subject a compound of formula I or a pharmaceutically acceptable salt thereof.

Another aspect of the present invention relates to a method of treating an allergic, immunological or inflammatory disease in a subject in need thereof, specially a human being, which comprises administering to said subject a compound of formula I or a pharmaceutically acceptable salt thereof. More preferably, the allergic, immunological or inflammatory disease is selected from respiratory diseases, ocular diseases, skin diseases, inflammatory bowel diseases, rheumatoid arthritis, multiple sclerosis, cutaneous lupus, systemic lupus erythematosus and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, dermatitis (e.g. atopic dermatitis), psoriasis, urticaria, pruritus, ulcerative colitis, Crohn's disease, rheumatoid arthritis, multiple sclerosis, cutaneous lupus, systemic lupus erythematosus and transplant rejection.

Another aspect of the present invention relates to a method of treating pain in a subject in need thereof, specially a human being, which comprises administering to said subject a compound of formula I or a pharmaceutically acceptable salt thereof. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a process for the preparation of a compound of formula I as defined above, comprising:

(a) reacting a compound of formula II with ammonia or an ammonia equivalent

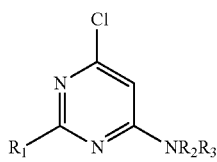

II wherein $R_1$, $R_2$ and $R_3$ have the meaning described above; or
(b) reacting a compound of formula VII with a compound of formula IV (or an amino-protected form thereof)

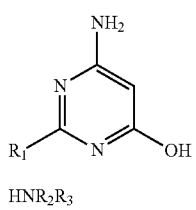

VII

IV wherein $R_1$, $R_2$ and $R_3$ have the meaning described above, followed if necessary by the removal of any protecting group that may be present; or (c) reacting a compound of formula VIIB with a compound of formula IV (or an amino-protected form thereof)

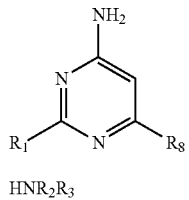

VIIB

IV wherein $R_8$ represents a leaving group and $R_1$, $R_2$ and $R_3$ have the meaning described above, followed if necessary by the removal of any protecting group that may be present; or
(d) when in a compound of formula I $R_1$ represents $R_1'$—$CH_2$—$CH_2$—, treating a compound of formula IX with a reducing agent

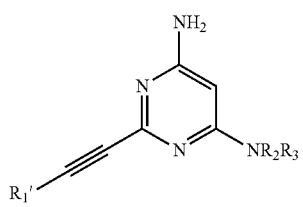

IX wherein $R_1'$ represents $C_{1-6}$ alkyl or $C_{3-8}$ cycloalkyl-$C_{0-4}$ alkyl or aryl-$C_{0-4}$ alkyl, wherein any alkyl group may be optionally substituted with one or more halogen groups and the $C_{3-8}$ cycloalkyl group may be optionally substituted with one or more substituents independently selected from $C_{1-4}$ alkyl, halogen and aryl, or $R_1'$ represents a group of formula (i) wherein n represents 2 and $R_4$ and $R_5$ represent H, or a group of formula (ii) wherein p represents 2 and $R_4$ and $R_5$ represent H; and $R_2$ and $R_3$ have the meaning described above; or
(e) transforming a compound of formula I into another compound of formula I in one or in several steps.

In the previous definitions, the term $C_{x-y}$ alkyl refers to a saturated linear or branched alkyl chain containing from x to y carbon atoms. Thus, a $C_{1-8}$ alkyl group refers to a linear or branched alkyl chain containing from 1 to 8 C atoms. A $C_{1-4}$ alkyl group refers to a linear or branched alkyl chain containing from 1 to 4 C atoms and includes methyl, ethyl, propyl, isopropyl, butyl, isobutyl, sec-butyl and tert-butyl. The term $C_0$ alkyl indicates that the alkyl group is absent.

A $C_{1-4}$ haloalkyl group means a group resulting from the substitution of one or more hydrogen atoms of a $C_{1-4}$ alkyl group with one or more halogen atoms (i.e. fluorine, chlorine, bromine or iodine) that may be the same or different. Examples include, amongst others, trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl and nonafluorobutyl.

A $C_{1-4}$ alkoxy group means a group of formula $C_{1-4}$ alkyl-O—, wherein the alkyl moiety has the same meaning as defined above. This term includes thus methoxy, ethoxy, propoxy, isopropoxy, butoxy, isobutoxy, sec-butoxy and tert-butoxy.

A $C_{1-4}$ haloalkoxy group means a group resulting from the substitution of one or more hydrogen atoms of a $C_{1-4}$ alkoxy group with one or more halogen atoms (i.e. fluorine, chlorine, bromine or iodine) that may be the same or different.

Examples include, amongst others, trifluoromethoxy, fluoromethoxy, 1-chloroethoxy, 2-chloroethoxy, 1-fluoroethoxy, 2-fluoroethoxy, 2-bromoethoxy, 2-iodoethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy and nonafluorobutoxy.

A $C_{3-8}$ cycloalkyl group, either as a group or as part of a $C_{3-8}$ cycloalkyl-$C_{0-y}$ alkyl group, relates to a saturated carbocyclic ring having from 3 to 8 carbon atoms that may be a monocyclic or a bridged bicyclic group. Examples include, amongst others, cyclopropyl, cyclobutyl, cyclopentyl, cyclohexyl, cycloheptyl, cyclooctyl, bicyclo[2.2.1]heptanyl and bicyclo[2.2.2]octanyl.

The term $C_{3-8}$ cycloalkyl-$C_{0-6}$ alkyl includes $C_{3-8}$ cycloalkyl and $C_{3-8}$ cycloalkyl-$C_{1-6}$ alkyl.

A $C_{3-8}$ cycloalkyl-$C_{1-6}$ alkyl group means a group resulting from the substitution of one or more hydrogen atoms of a $C_{1-6}$ alkyl group with one or more $C_{3-8}$ cycloalkyl groups, which may be the same or different. Preferably, the $C_{1-6}$ alkyl group is substituted with one or two $C_{3-8}$ cycloalkyl groups, and more preferably it is substituted with one $C_{3-8}$ cycloalkyl group. The $C_{3-8}$ cycloalkyl groups may substitute either one H atom on a C atom of the alkyl group, or two H atoms on a same C atom of the alkyl group (in which case the $C_{3-8}$ cycloalkyl group shares one C atom with the alkyl group), such as in the groups shown as examples below:

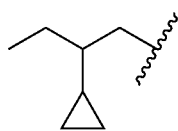

2-cyclopropybutyl
butyl group where 1 H atom on a C atom
is substituted with a cyclopropyl group

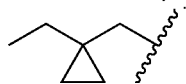

(1-ethyl-cyclopropyl)methyl
butyl group where 2 H
atoms on a same C atom
are substituted with a
cyclopropyl group Examples of $C_{3-8}$ cycloalkyl-$C_{1-6}$ alkyl groups include, amongst others, the groups cyclopropylmethyl, cyclobutylmethyl, cyclopentylmethyl, cyclohexylmethyl, cycloheptylmethyl, cyclooctylmethyl, bicyclo[2.2.1]heptanylmethyl, dicyclopropylmethyl, (1-methyl-cyclopropyl)methyl, (1-ethyl-cyclopropyl)methyl, (1-cyclopentylmethyl-cyclopropyl)methyl, 2-cyclopropylethyl, 2-cyclobutylethyl, 2-cyclopentylethyl, 2-cyclohexylethyl, 2,2-dicyclopropylethyl, 2-cyclohexyl-2-cyclopropyl-ethyl, 2-(1-methyl-cyclopropyl)ethyl, 1-cyclopropyl-1-methylethyl, 1-cyclopropylethyl, 1-cyclobutylethyl, 1-cyclopentylethyl, 1-cyclohexylethyl, 3-cyclopropylpropyl, 3-cyclobutylpropyl, 3-cyclopentylpropyl, 3-cyclohexylpropyl, 1-cyclopropyl-2-methylpropyl, 4-cyclopropylbutyl, 3-cyclopropylbutyl, 2-cyclopropylbutyl, 1-cyclopropylbutyl, 4-cyclobutylbutyl, 4-cyclopentylbutyl, 4-cyclohexylbutyl, 5-cyclopropylpentyl, and 6-cyclopropylhexyl.

When in the definition of a compound of formula I, it is indicated that a $C_{3-8}$ cycloalkyl group may be optionally substituted with one or more groups independently selected from $C_{1-4}$ alkyl, halogen and aryl, said substituents may be the same or different and may be located on any available carbon atom of the $C_{3-8}$ cycloalkyl group, including the carbon binding the cycle to the rest of the molecule.

The term aryl-$C_{0-4}$ alkyl includes aryl and aryl-$C_{1-4}$ alkyl.

An aryl-$C_{1-y}$ alkyl group means a group resulting from the substitution of a hydrogen atom of a $C_{1-y}$ alkyl group with an aryl group. When y is 4, examples of aryl-$C_{1-4}$ alkyl include, amongst others, the groups benzyl, 1-phenylethyl, 2-phenylethyl, 1-phenyl-1-methylethyl, 3-phenylpropyl, 4-phenylbutyl and 2-phenyl-1-methylpropyl, wherein the phenyl groups may be optionally substituted as indicated above in the definition of the term aryl.

As indicated above in the definition of $R_1$ regarding meanings (1) to (3) and in the definition of $R_6$, any alkyl group may be optionally substituted with one or more halogen groups. This refers to the $C_{1-8}$ alkyl group and the $C_{0-6}$ alkyl group that forms part of the $C_{3-8}$ cycloalkyl-$C_{3-8}$ alkyl group both in $R_1$ and $R_6$, as well as to the $C_{1-6}$ alkyl group that forms part of the aryl-$C_{1-6}$ alkyl group in $R_1$ and the $C_{0-4}$ alkyl group that forms part of the aryl-$C_{0-4}$ alkyl group in $R_6$.

As described above, $R_7$ represents a saturated monocyclic heterocyclic ring having from 4 to 7 ring atoms and containing one O atom and no other heteroatom. Said heterocyclic ring may be bound to the rest of the molecule via any available C atom. Examples of $R_7$ rings include, amongst others:

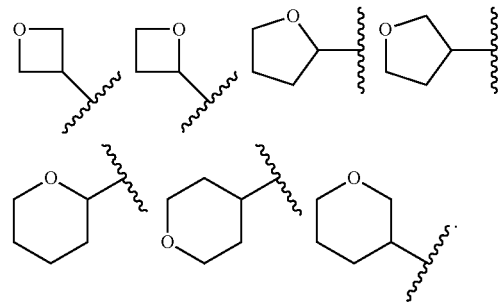

Any $R_7$ ring may be optionally substituted with one or more groups independently selected from $C_{1-4}$ alkyl and halogen, as described above, and said substituents may be placed in any available position on the ring.

A halogen group or its abbreviation halo means fluorine, chlorine, bromine or iodine. Preferred halogen groups are fluorine and chlorine, and more preferably fluorine.

An amino group in the definition of aryl means $NH_2$.

The term "saturated" refers to groups that do not contain any double or triple bond.

A "bridged bicyclic" group refers to a bicyclic system having two common atoms (bridgeheads) connecting three acyclic chains (bridges), so that the two bridges with the higher number of atoms form then the main ring and the bridge with the lower number of atoms is the "bridge".

In the definition of $NR_2R_3$, $R_2$ and $R_3$ together with the N atom to which they are bound can form a saturated 4- to 7-membered monocyclic heterocycle containing up to 2 N atoms and no other heteroatom. Examples include, among others, azetidinyl, pyrrolidinyl, piperidinyl, piperazinyl and homopiperazinyl.

In the definition of $NR_2R_3$, $R_2$ and $R_3$ together with the N atom to which they are bound can form a bridged bicyclic group having from 7 to 8 atoms. Said bridged bicyclic group can contain up to two N atoms and does not contain any other heteroatom. Examples include, among others, 2,5-diaza-bicyclo[2.2.1]heptanyl and 2,5-diaza-bicyclo[2.2.2]octanyl.

The term "fused bicyclic" group, in the definition of $NR_2R_3$, refers to a 8- to 12-membered bicyclic system consisting of two adjacent rings sharing two atoms in common. Said fused bicyclic group can contain up to two N atoms in any available position and does not contain any other heteroatom. Examples include, among others, octahydropyrrolo[3,4-b]pyridinyl, octahydropyrrolo[3,2-c]pyridinyl, octahydropyrrolo[1,2-a]pyrazinyl and octahydropyrrolo[3,4-c]pyrrolinyl.

As indicated above for the term $NR_2R_3$ in the definition of a compound of formula I, the above three types of saturated heterocyclic rings (monocyclic, bridged bicyclic and fused bicyclic) can be optionally substituted with one or more groups independently selected from $C_{1-4}$ alkyl and $NR_aR_b$, with the proviso that the heterocyclic group either contains 2 N atoms and is not substituted with an $NR_aR_b$ group, or contains 1 N atom and is substituted with one $NR_aR_b$ group. Thus, if the heterocyclic ring contains 1 N atom, then the ring must be substituted with one $NR_aR_b$ group and can additionally be optionally substituted with one or more $C_{1-4}$ alkyl groups. If the ring contains 2 N atoms, it can be optionally substituted with one or more $C_{1-4}$ alkyl groups while it cannot be substituted with any $NR_aR_b$ group. The substituents, if present, can be placed on any available position of the ring, including on a N atom in the case of $C_{1-4}$ alkyl groups.

When in a compound of formula I n represents 2 or 3 or p represents 2 and therefore there is more than one $R_4$ group and more than one $R_5$ group in said compound, each $R_4$ and each $R_5$ is independently selected from the list of possible meanings for said substituents indicated above in the definition of a compound of formula I and therefore these groups may be the same or different.

The expression "optionally substituted with one or more" means that a group can be substituted with one or more, preferably with 1, 2, 3 or 4 substituents, more preferably with 1 or 2 substituents, provided that said group has enough positions available susceptible of being substituted. These substituents can be the same or different, and can be placed on any available position.

Throughout the present specification, the expressions "treatment" of a disease, "treating" a disease and the like refer both to curative treatment as well as palliative treatment or prophylactic treatment of said disease. For purposes of this invention, beneficial or desired clinical results include, but are not limited to, alleviation or amelioration of one or more symptoms, diminishment of extent of disease, stabilized (i.e. not worsening) state of disease, preventing the disease from occurring in a patient that is predisposed or does not yet display symptoms of the disease, delay or slowing of disease progression, amelioration or palliation of the disease state, and remission (whether partial or total). Those in need of treatment include those already with the disease or disorder as well as those prone to have the disease or disorder or those in which the disease or disorder is to be prevented.

The invention thus relates to the compounds of formula I as defined above.

In another embodiment, the invention relates to compounds of formula I wherein $R_1$ represents:
(1) $C_{1-8}$ alkyl;
(2) $C_{3-8}$ cycloalkyl-$C_{0-6}$ alkyl; or
(3) aryl-$C_{1-6}$ alkyl;
wherein in groups (1) to (3) any alkyl group may be optionally substituted with one or more halogen groups and the $C_{3-8}$ cycloalkyl group may be optionally substituted with one or more substituents independently selected from $C_{1-4}$ alkyl, halogen and aryl.

In another embodiment, the invention relates to compounds of formula I wherein $R_1$ represents:
(1) $C_{4-6}$ alkyl;
(2) $C_{3-8}$ cycloalkyl-$C_{0-1}$ alkyl; or
(3) aryl-$C_{1-2}$ alkyl.

In another embodiment, the invention relates to compounds of formula I wherein $R_1$ represents $C_{1-8}$ alkyl or $C_{3-8}$ cycloalkyl-$C_{0-6}$ alkyl, wherein any alkyl group may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{1-8}$ alkyl or $C_{3-8}$ cycloalkyl-$C_{0-6}$ alkyl.

In another embodiment, the invention relates to compounds of formula I wherein $R_1$ represents $C_{1-8}$ alkyl or $C_{3-8}$ cycloalkyl-$C_{0-1}$ alkyl, wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{1-8}$ alkyl or $C_{3-8}$ cycloalkyl-$C_{0-1}$alkyl.

In another embodiment, the invention relates to compounds of formula I wherein $R_1$ represents $C_{4-6}$ alkyl or $C_{3-8}$ cycloalkyl-$C_{0-1}$ alkyl, wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{4-6}$ alkyl or $C_{3-8}$ cycloalkyl-$C_{0-1}$alkyl.

In another embodiment, the invention relates to compounds of formula I wherein $R_1$ represents isobutyl, 2,2-dimethylpropyl, cyclobutyl, cyclopentyl, cyclohexyl, cyclohexylmethyl or cyclopropylmethyl.

In another embodiment, the invention relates to compounds of formula I wherein $R_1$ represents $C_{1-8}$ alkyl or $C_{3-8}$ cycloalkyl-$C_1$ alkyl, wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{1-8}$ alkyl or $C_{3-8}$ cycloalkyl-$C_1$ alkyl.

In another embodiment, the invention relates to compounds of formula I wherein $R_1$ represents $C_{4-6}$ alkyl or $C_{3-8}$ cycloalkyl-$C_1$ alkyl.

In another embodiment, the invention relates to compounds of formula I wherein $R_1$ represents isobutyl, 2,2-dimethylpropyl or cyclopropylmethyl.

In another embodiment, the invention relates to compounds of formula I wherein $R_1$ represents $C_{1-8}$ alkyl optionally substituted with one or more halogen groups (preferably fluorine).

In another embodiment, the invention relates to compounds of formula I wherein $R_1$ represents $C_{1-8}$ alkyl.

In another embodiment, the invention relates to compounds of formula I wherein $R_1$ represents $C_{4-6}$ alkyl, preferably $C_{4-5}$ alkyl, and more preferably branched $C_{4-5}$ alkyl.

In another embodiment, the invention relates to compounds of formula I wherein $R_1$ represents isobutyl or 2,2-dimethylpropyl.

In another embodiment, the invention relates to compounds of formula I wherein $R_1$ represents isobutyl.

In another embodiment, the invention relates to compounds of formula I wherein $R_1$ represents 2,2-dimethylpropyl.

In another embodiment, the invention relates to compounds of formula I wherein $R_1$ represents $C_{3-8}$ cycloalkyl-$C_{0-6}$ alkyl, wherein the alkyl group may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{3-8}$ cycloalkyl-$C_{0-6}$ alkyl.

In another embodiment, the invention relates to compounds of formula I wherein $R_1$ represents $C_{3-8}$ cycloalkyl-$C_{0-1}$ alkyl, wherein the alkyl group may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_1$ represents $C_{3-8}$ cycloalkyl-$C_{0-1}$ alkyl.

In another embodiment, the invention relates to compounds of formula I wherein $R_1$ represents cyclobutyl, cyclopentyl, cyclohexyl, cyclohexylmethyl or cyclopropylmethyl.

In another embodiment, the invention relates to compounds of formula I wherein $R_1$ represents $C_{3-8}$ cycloalkyl-$C_{1-6}$ alkyl, wherein the alkyl group may be optionally substituted with one or more halogen groups (preferably fluorine) and the $C_{3-8}$ cycloalkyl may be optionally substituted with one or more substituents independently selected from $C_{1-4}$ alkyl, halogen (preferably fluorine) and aryl.

In another embodiment, the invention relates to compounds of formula I wherein $R_1$ represents $C_{3-8}$ cycloalkyl-$C_{1-6}$ alkyl.

In another embodiment, the invention relates to compounds of formula I wherein $R_1$ represents $C_{3-8}$ cycloalkyl-$C_1$ alkyl.

In another embodiment, the invention relates to compounds of formula I wherein $R_1$ represents cyclopropylmethyl.

In another embodiment, the invention relates to compounds of formula I wherein $R_1$ represents cyclohexylmethyl.

In another embodiment, the invention relates to compounds of formula I wherein $R_1$ represents $C_{3-8}$ cycloalkyl, which may be optionally substituted with one or more substituents independently selected from $C_{1-4}$ alkyl, halogen (preferably fluorine) and aryl.

In another embodiment, the invention relates to compounds of formula I wherein $R_1$ represents $C_{3-8}$ cycloalkyl, preferably $C_{4-6}$ cycloalkyl.

In another embodiment, the invention relates to compounds of formula I wherein $R_1$ represents cyclobutyl, cyclopentyl or cyclohexyl.

In another embodiment, the invention relates to compounds of formula I wherein $R_1$ represents aryl-$C_{1-6}$ alkyl, wherein the alkyl group may be optionally substituted with one or more halogen groups (preferably fluorine).

In another embodiment, the invention relates to compounds of formula I wherein $R_1$ represents aryl-$C_{1-2}$ alkyl, wherein the alkyl group may be optionally substituted with one or more halogen groups (preferably fluorine).

In another embodiment, the invention relates to compounds of formula I wherein $R_1$ represents aryl-$C_{1-6}$ alkyl, preferably aryl-$C_{1-2}$ alkyl.

In another embodiment, the invention relates to compounds of formula I wherein $R_1$ represents aryl-$C_{1-6}$ alkyl, wherein the alkyl group may be optionally substituted with one or more halogen groups (preferably fluorine) and aryl represents phenyl optionally substituted with one or more groups independently selected from halogen, $C_{1-4}$ alkoxy, $C_{1-4}$ haloalkoxy and cyano.

In another embodiment, the invention relates to compounds of formula I wherein $R_1$ represents (i).

In another embodiment, the invention relates to compounds of formula I wherein $R_1$ represents (ii).

In another embodiment, the invention relates to compounds of formula I wherein $R_4$ and $R_5$ are independently selected from H and $C_{1-4}$ alkyl, and additionally one of the $R_4$ or $R_5$ groups may represent aryl or $C_{3-8}$ cycloalkyl-$C_{0-6}$ alkyl.

In another embodiment, the invention relates to compounds of formula I wherein $R_4$ and $R_5$ are independently selected from H and $C_{1-4}$ alkyl, and additionally one of the $R_4$ or $R_5$ groups may represent aryl.

In another embodiment, the invention relates to compounds of formula wherein $R_4$ and $R_5$ are independently selected from H and $C_{1-4}$ alkyl.

In another embodiment, the invention relates to compounds of formula wherein $R_4$ and $R_5$ are independently selected from H and methyl.

In another embodiment, the invention relates to compounds of formula wherein $R_4$ and $R_5$ represent H.

In another embodiment, the invention relates to compounds of formula wherein one of the $R_4$ or $R_5$ groups represents aryl.

In another embodiment, the invention relates to compounds of formula wherein n represents 1 or 2.

In another embodiment, the invention relates to compounds of formula wherein p represents 0 or 1.

In another embodiment, the invention relates to compounds of formula wherein $R_6$ represents $C_{1-8}$ alkyl optionally substituted with one or more halogen groups (preferably fluorine).

In another embodiment, the invention relates to compounds of formula I wherein $R_6$ represents $C_{1-8}$ alkyl.

In another embodiment, the invention relates to compounds of formula I wherein $R_6$ represents $C_{3-8}$ cycloalkyl-$C_{0-6}$ alkyl, wherein the alkyl group may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_6$ represents $C_{3-8}$ cycloalkyl-$C_{0-1}$ alkyl, wherein the alkyl group may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl.

In another embodiment, the invention relates to compounds of formula I wherein $R_6$ represents $C_{3-8}$ cycloalkyl-$C_{0-1}$ alkyl.

In another embodiment, the invention relates to compounds of formula I wherein $R_6$ represents aryl-$C_{0-4}$ alkyl, wherein the alkyl group may be optionally substituted with one or more halogen groups (preferably fluorine).

In another embodiment, the invention relates to compounds of formula I wherein $R_6$ represents aryl-$C_{0-1}$ alkyl.

In another embodiment, the invention relates to the compounds of formula I wherein $R_2$ and $R_3$ form, together with the N atom to which they are bound, a saturated heterocyclic group selected from:
(i) a heterocyclic group which contains 2 N atoms and does not contain any other heteroatom, wherein said heterocyclic group can be optionally substituted with one or more $C_{1-4}$ alkyl groups; and
(ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;
wherein said heterocyclic groups (i) and (ii) can be 4- to 7-membered monocyclic, 7- to 8-membered bridged bicyclic or 8- to 12-membered fused bicyclic;
or $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups.

In another embodiment, the invention relates to compounds of formula I wherein $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to the compounds of formula I wherein $R_2$ and $R_3$ form, together with the N atom to which they are bound, a saturated heterocyclic group selected from:
(i) a heterocyclic group which contains 2 N atoms and does not contain any other heteroatom, wherein said heterocyclic group can be optionally substituted with one or more $C_{1-4}$ alkyl groups; and
(ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;
wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein $R_a$ and $R_b$ independently represent H or $C_{1-4}$ alkyl.

In another embodiment, the invention relates to the compounds of formula I wherein $R_a$ and $R_b$ independently represent H, methyl or ethyl.

In another embodiment, the invention relates to compounds of formula I wherein $R_a$ and $R_b$ independently represent H or methyl.

In another embodiment, the invention relates to the compounds of formula I wherein $R_a$ represents H and $R_b$ represents H or $C_{1-4}$ alkyl.

In another embodiment, the invention relates to the compounds of formula I wherein $R_a$ represents H and $R_b$ represents H, methyl or ethyl.

In another embodiment, the invention relates to the compounds of formula I wherein $R_a$ represents H and $R_b$ represents H or methyl.

In another embodiment, the invention relates to the compounds of formula I wherein $R_a$ represents H and $R_b$ represents $C_{1-4}$ alkyl.

In another embodiment, the invention relates to the compounds of formula I wherein $R_a$ represents H and $R_b$ represents methyl or ethyl.

In another embodiment, the invention relates to the compounds of formula I wherein $R_a$ represents H and $R_b$ represents methyl.

In another embodiment, the invention relates to compounds of formula I wherein $R_2$ and $R_3$ form, together with the N atom to which they are bound, a saturated heterocyclic group selected from:

(a)

(b)

(c)

(d)

(e)

(f)

-continued (g)

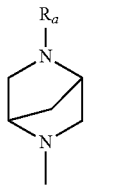

(h)

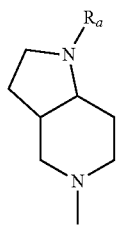

wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein $R_2$ and $R_3$ form, together with the N atom to which they are bound, a saturated heterocyclic group selected from (a) to (h), and $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein $R_2$ and $R_3$ form, together with the N atom to which they are bound, a saturated heterocyclic group selected from (a) and (b), wherein $R_a$ and $R_b$ have the meaning previously described for the compounds of formula I and $R_c$ represents H or $C_{1-4}$ alkyl, and preferably $R_c$ represents H.

In another embodiment, the invention relates to compounds of formula I wherein $R_2$ and $R_3$ form, together with the N atom to which they are bound, a saturated heterocyclic group selected from (a) and (b), and $R_a$, $R_b$ and $R_c$ independently represent H or $C_{1-4}$ alkyl, and preferably $R_a$, $R_b$ and $R_c$ independently represent H or methyl.

In another embodiment, the invention relates to compounds of formula I wherein $R_2$ and $R_3$ form, together with the N atom to which they are bound, a saturated heterocyclic group selected from (a) and (b), $R_a$ represents H, $R_b$ represents H or $C_{1-4}$ alkyl and $R_c$ represents H.

In another embodiment, the invention relates to compounds of formula I wherein $R_2$ and $R_3$ form, together with the N atom to which they are bound, a saturated heterocyclic group selected from (a) and (b), $R_a$ represents H, $R_b$ represents H or methyl and $R_c$ represents H.

In another embodiment, the invention relates to compounds of formula I wherein $R_2$ and $R_3$ form, together with the N atom to which they are bound, a saturated heterocyclic group selected from (a) and (b), $R_a$ represents H, $R_b$ represents methyl and $R_c$ represents H.

In another embodiment, the invention relates to compounds of formula I wherein $R_2$ and $R_3$ form, together with the N atom to which they are bound, a saturated heterocyclic group of formula (a)

(a)

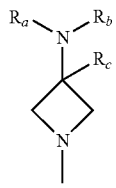

wherein $R_a$ and $R_b$ have the meaning previously described for the compounds of formula I and $R_c$ represents H or $C_{1-4}$ alkyl, and preferably $R_c$ represents H.

In another embodiment, the invention relates to the compounds of formula I wherein $R_2$ and $R_3$ form, together with the N atom to which they are bound, a saturated heterocyclic group of formula (a), and $R_a$, $R_b$ and $R_c$ independently represent H or $C_{1-4}$ alkyl, and preferably $R_a$, $R_b$ and $R_c$ independently represent H or methyl.

In another embodiment, the invention relates to the compounds of formula I wherein $R_2$ and $R_3$ form, together with the N atom to which they are bound, a saturated heterocyclic group of formula (a), $R_a$ represents H, $R_b$ represents H or $C_{1-4}$ alkyl and $R_c$ represents H.

In another embodiment, the invention relates to the compounds of formula I wherein $R_2$ and $R_3$ form, together with the N atom to which they are bound, a saturated heterocyclic group of formula (a), $R_a$ represents H, $R_b$ represents H or methyl and $R_c$ represents H.

In another embodiment, the invention relates to the compounds of formula I wherein $R_2$ and $R_3$ form, together with the N atom to which they are bound, a saturated heterocyclic group of formula (a), $R_a$ represents H, $R_b$ represents methyl and $R_c$ represents H.

In another embodiment, the invention relates to compounds of formula I wherein $R_2$ and $R_3$ form, together with the N atom to which they are bound, a saturated heterocyclic group of formula (b)

(b)

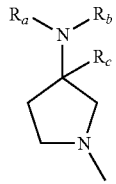

wherein $R_a$ and $R_b$ have the meaning previously described for the compounds of formula I and $R_c$ represents H or $C_{1-4}$ alkyl, and preferably $R_c$ represents H.

In another embodiment, the invention relates to the compounds of formula I wherein $R_2$ and $R_3$ form, together with the N atom to which they are bound, a saturated heterocyclic group of formula (b), and $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to the compounds of formula I wherein $R_2$ and $R_3$ form, together with the N atom to which they are bound, a saturated heterocyclic group of formula (b), $R_a$ represents H, $R_b$ represents H or $C_{1-4}$ alkyl and $R_c$ represents H.

In another embodiment, the invention relates to the compounds of formula I wherein $R_2$ and $R_3$ form, together with the N atom to which they are bound, a saturated heterocyclic group of formula (b), $R_a$ represents H, $R_b$ represents H or methyl and $R_c$ represents H.

In another embodiment, the invention relates to the compounds of formula I wherein $R_2$ and $R_3$ form, together with the N atom to which they are bound, a saturated heterocyclic group of formula (b), $R_a$ represents H, $R_b$ represents methyl and $R_c$ represents H.

In another embodiment, the invention relates to compounds of formula I wherein $R_2$ represents H or $C_{1-4}$ alkyl and $R_3$ represents azetidinyl, pyrrolidinyl, piperidinyl or azepanyl, which may be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents $C_{1-8}$ alkyl or $C_{3-8}$ cycloalkyl-$C_{3-8}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group selected from:
(i) a heterocyclic group which contains 2 N atoms and does not contain any other heteroatom, wherein said heterocyclic group can be optionally substituted with one or more $C_{1-4}$ alkyl groups; and
(ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;
wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents $C_{1-8}$ alkyl or $C_{3-8}$ cycloalkyl-$C_{3-8}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group selected from (a) to (h), and $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{1-8}$ alkyl or $C_{3-8}$ cycloalkyl-$C_{3-8}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group selected from (a) and (b), and $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, and preferably $R_a$, $R_b$ and $R_c$ independently represent H or methyl, and more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{1-8}$ alkyl or $C_{3-8}$ cycloalkyl-$C_{0-6}$ alkyl, preferably $C_{4-6}$ alkyl or $C_{3-8}$ cycloalkyl-$C_{0-1}$ alkyl, and more preferably isobutyl, 2,2-dimethylpropyl or cyclopropylmethyl; wherein the alkyl groups may be optionally substituted with one or more halogen groups (preferably fluorine) and the $C_{3-8}$ cycloalkyl group may be optionally substituted with one or more substituents independently selected from $C_{1-4}$ alkyl, halogen (preferably fluorine) and aryl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{1-8}$ alkyl optionally substituted by one or more halogen groups (preferably fluorine); and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents $C_{1-8}$ alkyl optionally substituted with one or more halogen groups (preferably fluorine); and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group selected from (a) to (h), wherein $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{1-8}$ alkyl optionally substituted with one or more halogen groups (preferably fluorine); and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents $C_{4-6}$ alkyl, preferably isobutyl or 2,2-dimethylpropyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-y.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group selected from (a) to (h), and $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{4-6}$ alkyl, preferably isobutyl or 2,2-dimethylpropyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents isobutyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents isobutyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents isobutyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group selected from (a) to (h), wherein $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents isobutyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents 2,2-dimethylpropyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents 2,2-dimethylpropyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents 2,2-dimethylpropyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group selected from (a) to (h), and $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents 2,2-dimethylpropyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents $C_{3-8}$ cycloalkyl-$C_1$ alkyl and more preferably cyclopropylmethyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group selected from (a) to (h), wherein $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{3-8}$ cycloalkyl-$C_1$ alkyl and more preferably cyclopropylmethyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group selected from (a) to (h), wherein $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents $C_{3-8}$ cycloalkyl, preferably $C_{4-6}$ cycloalkyl and more preferably cyclobutyl, cyclopentyl or cyclohexyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group that can be 4- to 7-membered monocyclic, 7- to 8-membered bridged bicyclic or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group selected from:

(i) a heterocyclic group which contains 2 N atoms and does not contain any other heteroatom, wherein said heterocyclic group can be optionally substituted with one or more $C_{1-4}$ alkyl groups; and (ii) a heterocyclic group which contains 1 N atom and does not contain any other heteroatom, wherein said heterocyclic group is substituted with one $NR_aR_b$ group and can be optionally substituted with one or more $C_{1-4}$ alkyl groups;

wherein said heterocyclic groups (i) and (ii) can be 4- to 7-membered monocyclic, 7- to 8-membered bridged bicyclic or 8- to 12-membered fused bicyclic.

In another embodiment, the invention relates to compounds of formula I wherein:

$R_1$ represents aryl-$C_{1-6}$ alkyl, preferably aryl-$C_{1-2}$ alkyl; and $R_2$ represents H or $C_{1-4}$ alkyl, and $R_3$ represents azetidinyl, pyrrolidinyl, piperidinyl or azepanyl, which can be optionally substituted with one or more $C_{1-4}$ alkyl groups, and preferably $R_2$ represents H and $R_3$ represents 1-methyl-pyrrolidin-3-yl.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group selected from (a) to (h), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group selected from (a) to (h), wherein $R_a$, $R_b$ and $R_c$ independently represent H or $C_{1-4}$ alkyl, preferably $R_a$, $R_b$ and $R_c$ independently represent H or methyl, and more preferably $R_a$ and $R_b$ independently represent H or methyl and $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group selected from (a) and (b), wherein $R_a$ and $R_b$ have the meaning described above for compounds of formula I and $R_c$ represents H or $C_{1-4}$ alkyl and preferably $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group selected from (a) and (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group of formula (a), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group of formula (b), wherein $R_a$ and $R_b$ have the meaning described above for compounds of formula I and $R_c$ represents H or $C_{1-4}$ alkyl, and preferably $R_c$ represents H.

In another embodiment, the invention relates to compounds of formula I wherein:

$R_1$ represents aryl-$C_{1-6}$ alkyl, preferably aryl-$C_{1-2}$ alkyl; and $R_2$ and $R_3$ form, together with the N atom to which they are bound, a saturated heterocyclic group of formula (b), wherein $R_a$, $R_b$ and $R_c$ independently represent H or $C_{1-4}$ alkyl, preferably $R_a$, $R_b$ and $R_c$ independently represent H or methyl, more preferably $R_a$ and $R_b$ independently represent H or methyl and $R_c$ represents H, and still more preferably $R_a$ represents H, $R_b$ represents methyl and $R_c$ represents H.

Moreover, the present invention includes all possible combinations of the particular and preferred embodiments described above for the compounds of formula I.

In an additional embodiment, the invention relates to a compound of formula I selected from:

2-Isobutyl-6-((3R)-3-(methylamino)pyrrolidin-1-yl)pyrimidin-4-amine;

2-Cyclohexylmethyl-6-((3R)-3-(methylamino)pyrrolidin-1-yl)pyrimidin-4-amine;

2-(4-Fluorobenzyl)-6-(3-(methylamino)azetidin-1-yl)pyrimidin-4-amine;

2-Isobutyl-6-(3-(methylamino)azetidin-1-yl)pyrimidin-4-amine;

2-Cyclopropyl-6-(3-(methylamino)azetidin-1-yl)pyrimidin-4-amine;

2-tert-Butyl-6-(3-(methylamino)azetidin-1-yl)pyrimidin-4-amine;

2-Isopropyl-6-(3-(methylamino)azetidin-1-yl)pyrimidin-4-amine;

2-(Cyclopropylmethyl)-6-(3-(methylamino)azetidin-1-yl)pyrimidin-4-amine;

6-(3-(Methylamino)azetidin-1-yl)-2-(phenoxymethyl)pyrimidin-4-amine;

2-Cyclopropyl-6-((3R)-3-(methylamino)pyrrolidin-1-yl)pyrimidin-4-amine;

2-tert-Butyl-6-((3R)-3-(methylamino)pyrrolidin-1-yl)pyrimidin-4-amine;

2-Isopropyl-6-((3R)-3-(methylamino)pyrrolidin-1-yl)pyrimidin-4-amine;

6-((3R)-3-(Methylamino)pyrrolidin-1-yl)-2-(phenoxymethyl)pyrimidin-4-amine;

6-(3-Aminoazetidin-1-yl)-2-isobutylpyrimidin-4-amine;

2-Isobutyl-6-(3-methyl-3-(methylamino)azetidin-1-yl)pyrimidin-4-amine;

6-((3R)-3-aminopyrrolidin-1-yl)-2-isobutylpyrimidin-4-amine;

2-Cyclobutyl-6-(3-(methylamino)azetidin-1-yl)pyrimidin-4-amine;

2-Cyclobutyl-6-((3R)-3-(methylamino)pyrrolidin-1-yl)pyrimidin-4-amine;

2-Cyclopentyl-6-(3-(methylamino)azetidin-1-yl)pyrimidin-4-amine;
2-Cyclopentyl-6-((3R)-3-(methylamino)pyrrolidin-1-yl)pyrimidin-4-amine;
2-(2,2-Dimethylpropyl)-6-(3-(methylamino)azetidin-1-yl)pyrimidin-4-amine;
2-(2,2-Dimethylpropyl)-6-((3R)-3-(methylamino)pyrrolidin-1-yl)pyrimidin-4-amine;
2-(2-Cyclopentylethyl)-6-((3R)-3-(methylamino)pyrrolidin-1-yl)pyrimidin-4-amine;
2-Cyclohexylmethyl-6-(3-(methylamino)azetidin-1-yl)pyrimidin-4-amine;
2-Cyclopropylmethyl-6-((3R)-3-(methylamino)pyrrolidin-1-yl)pyrimidin-4-amine;
2-Cyclohexyl-6-(3-(methylamino)azetidin-1-yl)pyrimidin-4-amine;
2-Cyclohexyl-6-((3R)-3-(methylamino)pyrrolidin-1-yl)pyrimidin-4-amine; and
2-(4-Fluorobenzyl)-6-(3R)-3-(methylamino)pyrrolidin-1-yl)pyrimidin-4-amine,
or a salt thereof.

In an additional embodiment, the invention relates to a compound of formula I selected from:
2-Isobutyl-6-((3R)-3-(methylamino)pyrrolidin-1-yl)pyrimidin-4-amine;
2-Isobutyl-6-(3-(methylamino)azetidin-1-yl)pyrimidin-4-amine;
2-tert-Butyl-6-(3-(methylamino)azetidin-1-yl)pyrimidin-4-amine;
2-Isopropyl-6-(3-(methylamino)azetidin-1-yl)pyrimidin-4-amine;
2-tert-Butyl-6-((3R)-3-(methylamino)pyrrolidin-1-yl)pyrimidin-4-amine;
2-Isopropyl-6-((3R)-3-(methylamino)pyrrolidin-1-yl)pyrimidin-4-amine;
2-Isobutyl-6-(3-methyl-3-(methylamino)azetidin-1-yl)pyrimidin-4-amine;
6-(3-Aminoazetidin-1-yl)-2-isobutylpyrimidin-4-amine;
6-((3R)-3-aminopyrrolidin-1-yl)-2-isobutylpyrimidin-4-amine;
2-(2,2-dimethylpropyl)-6-(3-(methylamino)azetidin-1-yl)pyrimidin-4-amine; and
2-(2,2-dimethylpropyl)-6-(3R)-3-(methylamino)pyrrolidin-1-yl)pyrimidin-4-amine;
or a salt thereof.

In an additional embodiment, the invention relates to a compound of formula I selected from:
2-Isobutyl-6-((3R)-3-(methylamino)pyrrolidin-1-yl)pyrimidin-4-amine;
2-Isobutyl-6-(3-(methylamino)azetidin-1-yl)pyrimidin-4-amine;
2-Isobutyl-6-(3-methyl-3-(methylamino)azetidin-1-yl)pyrimidin-4-amine;
6-(3-Aminoazetidin-1-yl)-2-isobutylpyrimidin-4-amine;
6-((3R)-3-aminopyrrolidin-1-yl)-2-isobutylpyrimidin-4-amine;
2-(2,2-dimethylpropyl)-6-(3-(methylamino)azetidin-1-yl)pyrimidin-4-amine; and
2-(2,2-dimethylpropyl)-6-(3R)-3-(methylamino)pyrrolidin-1-yl)pyrimidin-4-amine;
or a salt thereof.

In an additional embodiment, the invention relates to a compound of formula I selected from:
2-Isobutyl-6-((3R)-3-(methylamino)pyrrolidin-1-yl)pyrimidin-4-amine;
2-Isobutyl-6-(3-(methylamino)azetidin-1-yl)pyrimidin-4-amine;
2-(2,2-dimethylpropyl)-6-(3-(methylamino)azetidin-1-yl)pyrimidin-4-amine; and
2-(2,2-dimethylpropyl)-6-(3R)-3-(methylamino)pyrrolidin-1-yl)pyrimidin-4-amine;
or a salt thereof.

In an additional embodiment, the invention relates to a compound of formula I selected from:
2-Cyclohexylmethyl-6-((3R)-3-(methylamino)pyrrolidin-1-yl)pyrimidin-4-amine;
2-Cyclohexylmethyl-6-(3-(methylamino)azetidin-1-yl)pyrimidin-4-amine;
2-(Cyclopropylmethyl)-6-(3-(methylamino)azetidin-1-yl)pyrimidin-4-amine;
2-Cyclopropylmethyl-6-((3R)-3-(methylamino)pyrrolidin-1-yl)pyrimidin-4-amine; and
2-(2-Cyclopentylethyl)-6-((3R)-3-(methylamino)pyrrolidin-1-yl)pyrimidin-4-amine,
or a salt thereof.

In an additional embodiment, the invention relates to a compound of formula I selected from:
2-Cyclopropyl-6-(3-(methylamino)azetidin-1-yl)pyrimidin-4-amine;
2-Cyclopropyl-6-((3R)-3-(methylamino)pyrrolidin-1-yl)pyrimidin-4-amine;
2-Cyclobutyl-6-(3-(methylamino)azetidin-1-yl)pyrimidin-4-amine;
2-Cyclobutyl-6-((3R)-3-(methylamino)pyrrolidin-1-yl)pyrimidin-4-amine;
2-Cyclopentyl-6-(3-(methylamino)azetidin-1-yl)pyrimidin-4-amine;
2-Cyclopentyl-6-((3R)-3-(methylamino)pyrrolidin-1-yl)pyrimidin-4-amine;
2-Cyclohexyl-6-(3-(methylamino)azetidin-1-yl)pyrimidin-4-amine; and
2-Cyclohexyl-6-((3R)-3-(methylamino)pyrrolidin-1-yl)pyrimidin-4-amine;
or a salt thereof.

In an additional embodiment, the invention relates to a compound of formula I selected from:
2-(4-Fluorobenzyl)-6-(3-(methylamino)azetidin-1-yl)pyrimidin-4-amine; and
2-(4-Fluorobenzyl)-6-(3R)-3-(methylamino)pyrrolidin-1-yl)pyrimidin-4-amine;
or a salt thereof.

In an additional embodiment, the invention relates to compounds according to formula I that provide more than 50% inhibition of histamine $H_4$ receptor activity at 10 µM, more preferably at 1 µM and even more preferably at 0.1 µM, in an $H_4$ receptor assay such as the one described in examples 29 or 30.

The compounds of the present invention contain one or more basic nitrogens and may, therefore, form salts with organic or inorganic acids. Examples of these salts include: salts with inorganic acids such as hydrochloric acid, hydrobromic acid, hydroiodic acid, nitric acid, perchloric acid, sulfuric acid or phosphoric acid; and salts with organic acids such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, among others.

There is no limitation on the type of salt that can be used, provided that these are pharmaceutically acceptable when used for therapeutic purposes. The term pharmaceutically acceptable salt refers to those salts which are, according to medical judgement, suitable for use in contact with the tissues of humans and other mammals without undue toxicity, irritation, allergic response and the like. Pharmaceutically acceptable salts are well known in the art.

The salts of a compound of formula I can be obtained during the final isolation and purification of the compounds of the invention or can be prepared by treating a compound of formula I with a sufficient amount of the desired acid to give the salt in a conventional manner. The salts of the compounds of formula I can be converted into other salts of the compounds of formula I by ion exchange using ion exchange resins.

The compounds of formula I and their salts may differ in some physical properties but they are equivalent for the purposes of the present invention. All salts of the compounds of formula I are included within the scope of the invention.

The compounds of the present invention may form complexes with solvents in which they are reacted or from which they are precipitated or crystallized. These complexes are known as solvates. As used herein, the term solvate refers to a complex of variable stoichiometry formed by a solute (a compound of formula I or a salt thereof) and a solvent. Examples of solvents include pharmaceutically acceptable solvents such as water, ethanol and the like. A complex with water is known as a hydrate. Solvates of compounds of the invention (or of salts thereof), including hydrates, are included within the scope of the invention.

The compounds of formula I may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula I, including all polymorphic forms ("polymorphs") thereof, are included within the scope of the invention.

Some of the compounds of the present invention may exist as several optical isomers and/or several diastereoisomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on the products of formula I. Optically pure isomers can also be individually obtained using enantiospecific synthesis. The present invention covers all individual isomers as well as mixtures thereof (for example racemic mixtures or mixtures of diastereomers), whether obtained by synthesis or by physically mixing them.

The compounds of formula I can be obtained by following the processes described below. As it will be obvious to one skilled in the art, the exact method used to prepare a given compound may vary depending on its chemical structure. Moreover, in some of the processes described below it may be necessary or advisable to protect the reactive or labile groups with conventional protecting groups. Both the nature of these protecting groups and the procedures for their introduction or removal are well known in the art (see for example Greene T. W. and Wuts P. G. M, "Protective Groups in Organic Synthesis", John Wiley & Sons, 3$^{rd}$ edition, 1999). Unless otherwise stated, in the methods described below the meanings of the different substituents are the meanings described above with regard to a compound of formula I.

In general, the compounds of formula I can be obtained by reacting a compound of formula II with ammonia or an ammonia equivalent, as shown in the following scheme. By ammonia equivalent it is meant a protected form of ammonia.

Any known ammonia equivalent can be used, such as benzophenoneimine, benzylamine or benzhydrylamine, preferably benzophenoneimine.

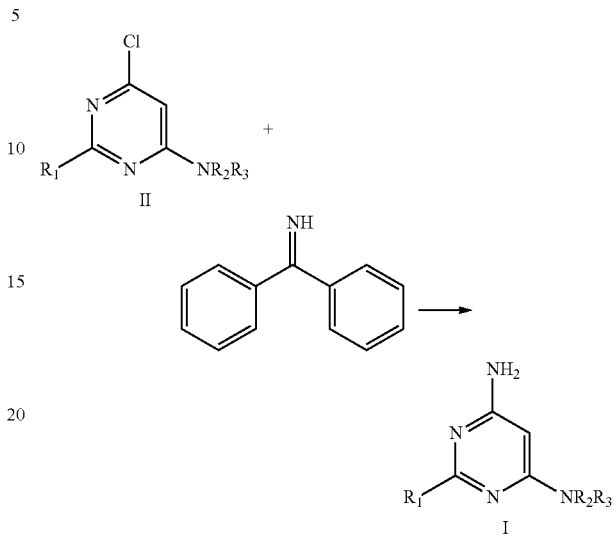

wherein $R_1$, $R_2$ and $R_3$ have the meaning described above for a compound of formula I.

The reaction between the compounds of formula II and benzophenoneimine may be carried out in the presence of a palladium catalyst, such as for example palladium diacetate and preferably tris(dibenzylideneacetone)dipalladium(0), a phosphine-type ligand, preferably 2,2'-bis(diphenylphosphino)-1,1'-binaphthyl, and a base, preferably sodium tert-butoxide. The reaction may be carried out in a solvent such as 1,4-dioxane, 1,2-dimethoxyethane or N,N-dimethylformamide, and preferably in toluene, and at a temperature comprised between room temperature and the reflux temperature, preferably at 85° C. The reaction mixture is then treated with a strong acid, preferably aqueous hydrochloric acid, in a suitable solvent, preferably tetrahydrofuran, in order to hydrolyse the imino group to the amino group present in the compounds of formula I.

When using ammonia or other amines that are precursors of ammonia such as benzylamine or benzhydrylamine, the reaction may be carried out thermally in a suitable solvent such as ethanol, butanol, acetonitrile or dimethylsulphoxide, among others, and heating; or alternatively, a catalyst may be used such as copper sulfate when using ammonia or a palladium catalyst when using benzylamine or benzhydrylamine. In this latter case, a deprotection step such as catalytic hydrogenation will be necessary to unmask the amino function.

The compounds of formula II can be obtained by reacting a compound of formula III with a compound of formula IV, as shown in the following scheme:

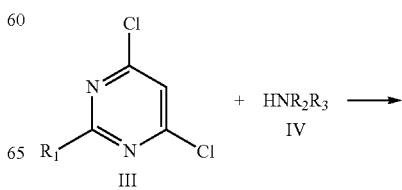

-continued

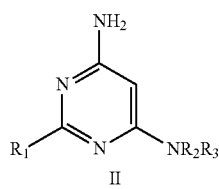

wherein $R_1$, $R_2$ and $R_3$ have the meaning described above for a compound of formula I.

The reaction between compounds of formula III and IV can be carried out in a suitable solvent such as ethanol, methanol, butanol, N,N-dimethylformamide, dimethylsulphoxide, tetrahydrofuran or toluene, preferably ethanol, in the presence of a base, including organic amines such as triethylamine, N,N-diisopropylethylamine, dimethylaniline and diethylaniline among others, preferably N,N-diisopropylethylamine, and heating, preferably at a temperature comprised between 50 and 100° C. The heating may be thermal or by irradiating with microwaves at a wattage that allows reaching the temperature mentioned above.

Alternatively, the compounds of formula I can be obtained from the compounds of formula III, by changing the order of the steps in the synthetic sequence, i.e. first reacting III with benzophenoneimine or ammonia (or any other known equivalent thereof) to give a compound of formula IIB and subsequently reacting a compound of formula IIB with an amine of formula IV, as shown in the following scheme:

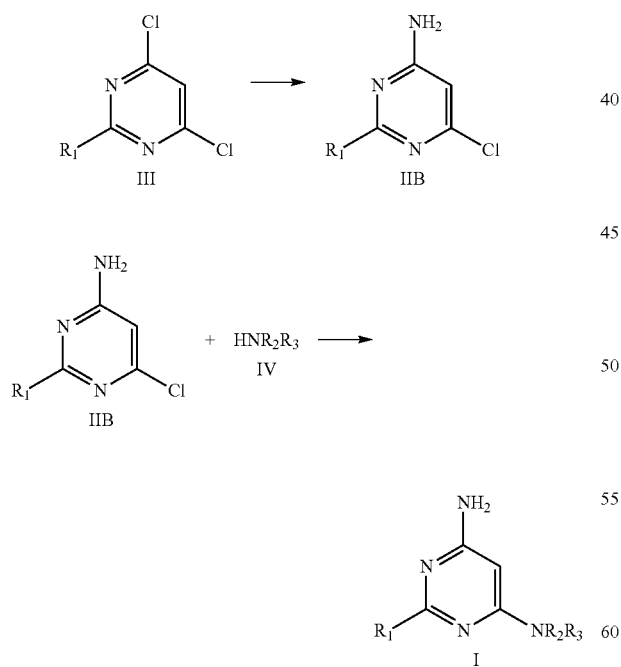

wherein $R_1$, $R_2$ and $R_3$ have the meaning described above for a compound of formula I.

In the case of using benzophenoneimine, the transformation of III into IIB may be carried out under palladium catalysis, e.g. using the conditions mentioned above to react a compound of formula II with benzophenoneimine. In the case ammonia or an equivalent amine is used, the reaction conditions to be used would be those described above for the reaction between a compound of formula III and a compound of formula IV.

The reaction between the compounds of formula IIB and IV can be carried out in the conditions described above for the reaction between a compound of formula III and a compound of formula IV, the preferred solvent being methanol or ethanol, and heating, preferably at reflux. The heating may be thermal or by irradiating with microwaves at a wattage that allows reaching the temperature mentioned above.

In general, before conducting the reaction between the compounds of formulas III and IV, or IIB and IV, the amino substituents of the compounds of formula IV are protected in order to prevent the formation of side products. Similarly, the amino group of the compounds of formula IIB can also be protected if necessary. Any suitable protective group may be used, such as for example a tert-butoxycarbonyl (Boc) group. A subsequent deprotection step may be necessary when the amino substituents of the compounds of formulae IV and/or IIB are protected, which is carried out under standard conditions. When the protective group is Boc, the deprotection can be conducted directly upon the crude product obtained by adding a solution of a strong acid such as HCl in a suitable solvent such as 1,4-dioxane, diethyl ether or methanol, or trifluoroacetic acid in dichloromethane.

The compounds of formula III can be obtained from the compounds of formula V, as shown in the following scheme:

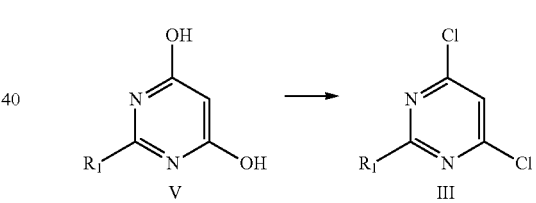

wherein $R_1$ has the meaning described above for a compound of formula I.

The —OH group from a compound of formula V may be transformed into a leaving group such as halogen, preferably chlorine, by reaction with a halogenating agent such as POCl$_3$, optionally in the presence of a suitable solvent, or POCl$_3$/PCl$_5$ or N,N-dimethylformamide/oxalyl chloride mixtures in the presence of a suitable solvent such as 1,4-dioxane or 1,2-dichloroethane, and preferably POCl$_3$. The reaction is performed by heating, preferably under reflux.

The compounds of formula V can be obtained by reacting an amidine of formula VI with diethyl malonate, as shown in the following scheme:

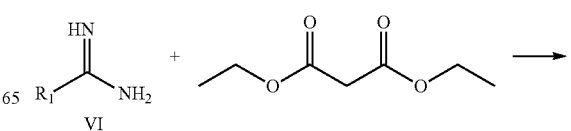

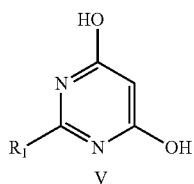

wherein $R_1$ has the meaning described above for a compound of formula I.

The reaction takes place in the presence of a base such as sodium tert-butoxide or sodium methoxide and preferably sodium ethoxide, in a suitable solvent, preferably ethanol. The reaction can be performed by heating at a suitable temperature usually comprised between room temperature and the reflux temperature, preferably under reflux.

The compounds of formula IV are commercial or can be obtained using procedures described in the literature.

The compounds of formula VI are commercial or may be easily obtained from commercial nitriles by known methods (see *Tetrahedron Letters* 1995, 36, 48, 8761).

Alternatively, the compounds of formula I may be obtained by reaction of a hydroxy derivative of formula VII with an amine of formula IV as shown in the following scheme:

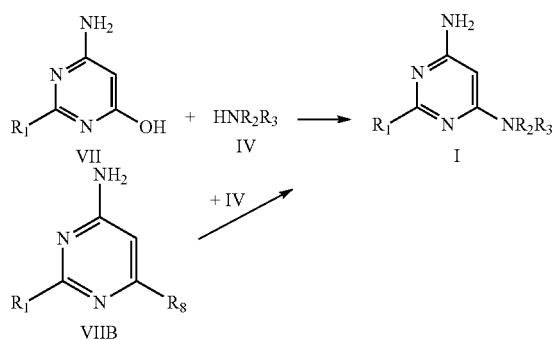

wherein $R_1$, $R_2$ and $R_3$ have the meaning described above for a compound of formula I, and $R_8$ represents a leaving group such as halogen, triflate or tosylate. When $R_8$ represents a chlorine atom, the compounds of formula VIIB correspond to compounds of formula IIB.

The reaction between the compounds of formula VII and IV may be carried out using a coupling agent such as for example PyBOP (benzotriazol-1-yl-oxytripyrrolidinophosphonium hexafluorophosphate) in a suitable solvent, preferably in acetonitrile or mixtures of acetonitrle and 1,4-dioxane, in the presence of a base, preferably triethylamine and at a temperature comprised between room temperature and the reflux temperature.

Alternatively, the compounds of formula I can be obtained by reacting a compound of formula IV with a reactive derivative of a compound of formula VII (VIIB) obtained by conversion of the hydroxy group present in a compound VII into a leaving group such as halogen, triflate o tosylate, preferably chlorine.

Thus, the —OH group from a compound of formula VII may be transformed into a leaving group such as halogen, preferably chlorine, by reaction with a halogenating agent such as POCl$_3$ (see *Journal of Medicinal Chemistry* 1998, 41, 3793), optionally in the presence of a suitable solvent, or POCl$_3$/PCl$_5$ or N,N-dimethylformamide/oxalyl chloride mixtures in the presence of a suitable solvent such as 1,4-dioxane or 1,2-dichloroethane. The reaction is performed by heating, preferably at a temperature comprised between 100° C. and 140° C. Similarly, the hydroxy group of a compound of formula VII can be transformed into a triflate group by reaction with trifluoromethanesulphonic anhydride in the presence of pyridine, or into a tosylate group by reaction with p-toluenesulfonyl chloride in the presence of a solvent such as dichloromethane and a base such as triethylamine.

The reactive derivative of a compound of formula VII thus obtained (VIIB) is then allowed to react with a compound of formula IV in order to give a compound of formula I. The reaction is performed in a suitable solvent such as ethanol, methanol, butanol, N,N-dimethylformamide, dimethylsulphoxide, tetrahydrofuran, acetonitrile or toluene, preferably methanol or ethanol, in the presence of a base, including organic amines such as triethylamine, N,N-diisopropylethylamine, dimethylaniline and diethylaniline among others, and heating, preferably at 100° C. or reflux. The heating may be thermal or by irradiating with microwaves at a wattage that allows reaching the temperature mentioned above.

The compounds of formula VII may be obtained by reacting an amidine of formula VI with ethyl cyanoacetate (see *Journal of Medicinal Chemistry* 1998, 41, 3793) or with ethyl 3-ethoxy-3-iminopropionate (see *European Journal of Medicinal Chemistry* 1996, 31, 4, 273), as shown in the following scheme:

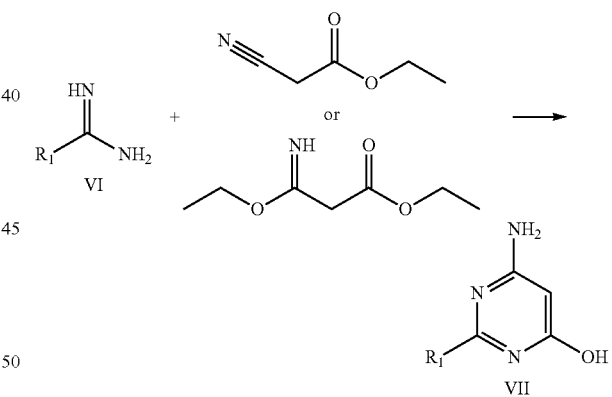

wherein $R_1$ has the meaning described above for a compound of formula I.

Alternatively, the compounds of formula IIB may be obtained by reacting a zinc derivative of formula VIII with 4-amino-2,6-dichloropyrimidine (which is commercially available), as shown in the following scheme:

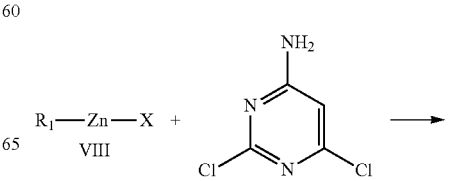

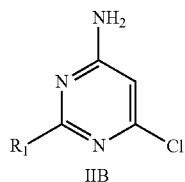

IIB wherein $R_1$ has the meaning described for a compound of formula I, and X represents halogen.

The reaction between the compounds of formula VIII and 4-amino-2,6-dichloropyrimidine may be carried out in the presence of a palladium catalyst, preferably palladium diacetate, and a phosphine-type ligand, preferably tri-tert-butylphosphine. The reaction may be carried out in a suitable solvent such as tetrahydrofuran, 1,4-dioxane, 1,2-dimethoxyethane or 1-methyl-2-pyrrolidinone, preferably in a mixture of tetrahydrofuran and 1-methyl-2-pyrrolidinone, and at a temperature comprised between room temperature and the reflux temperature, preferably at 100° C.

The compounds of formula VIII are commercial or may be easily obtained from commercial compounds using standard procedures.

Alternatively, the compounds of formula I wherein $R_1$ represents $R_1'$—$CH_2$—$CH_2$— (i.e. compounds of formula I') can be obtained by reduction of a compound of formula IX, as shown in the following scheme:

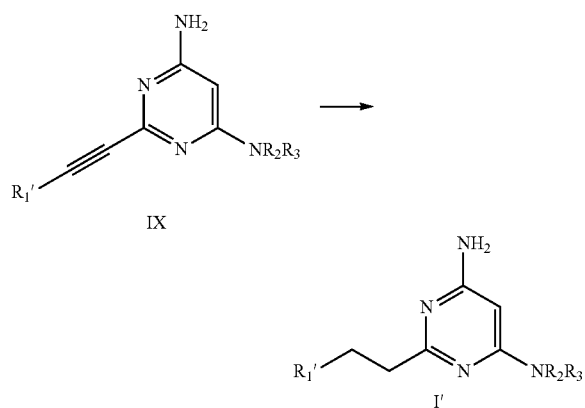

wherein $R_1'$ represents $C_{1-6}$ alkyl or $C_{3-8}$ cycloalkyl-$C_{0-4}$ alkyl or aryl-$C_{0-4}$ alkyl, wherein any alkyl group may be optionally substituted with one or more halogen groups and the $C_{3-8}$ cycloalkyl group may be optionally substituted with one or more substituents independently selected from $C_{1-4}$ alkyl, halogen and aryl, or $R_1'$ represents a group of formula (i) wherein n represents 2 and $R_4$ and $R_5$ represent H, or a group of formula (ii) wherein p represents 2 and $R_4$ and $R_5$ represent H; and $R_2$ and $R_3$ have the meaning described above for compounds of formula I.

The reaction takes place in a reducing medium that preferably consists of a source of hydrogen, preferably in gas form ($H_2$) and a metal catalyst, preferably palladium in homogeneous or heterogeneous form, and more preferably Pd/C, in a suitable solvent such as for example methanol or ethanol. The reaction can be performed by heating at a suitable temperature usually comprised between room temperature and the reflux temperature, preferably at room temperature.

The compounds of formula IX can be obtained by reacting a compound of formula X with a compound of formula IV, as shown in the following scheme:

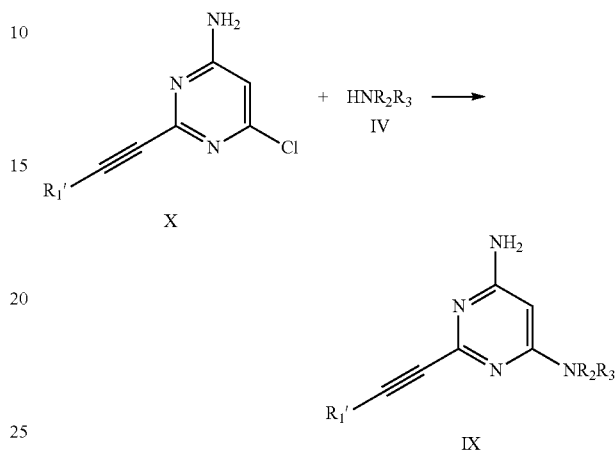

wherein $R_1'$ has the meaning described above and $R_2$ and $R_3$ have the meaning described for compounds of formula I.

The reaction may be performed under the same conditions described above for the reaction between compounds IIB or VIIB and IV to provide a compound of formula I.

Similarly to the preparation of the compounds of formula I described above from compounds of formula IIB or III and IV, the amino substituents of the compounds of formula IV should be protected in order to prevent the formation of side products, before carrying out the reaction between compounds of formulae X and IV. Similarly, the amino group of the compounds of formula X can also be protected if necessary. A subsequent deprotection step may be necessary when the amino substituents of the compounds of formulae IV and/or X are protected, which is carried out under standard conditions.

The compounds of formula X may in turn be obtained by the coupling reaction of an alkyne of formula XI with commercially available 4-amino-2,6-dichloropyrimidine, as shown in the following scheme:

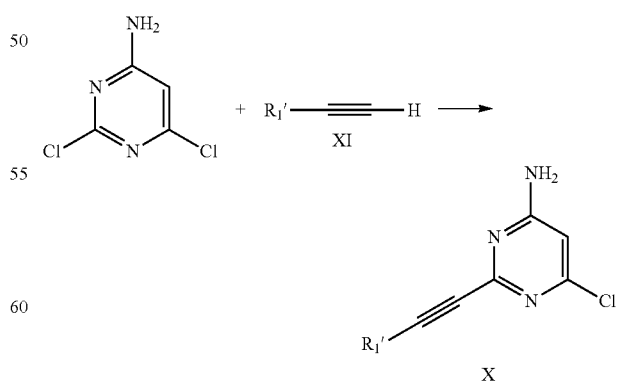

wherein $R_1'$ has the meaning described above.

The reaction may be carried out under Sonogashira conditions, using a palladium catalyst such as for example tetrakis (triphenylphosphino)palladium(0) (Pd(PPh$_3$)$_4$), or bis(triphenylphosphino)dichloropalladium(II) (Pd(Ph$_3$P)$_2$Cl$_2$) in the presence of triphenylphospine, a Cu (I) catalyst as a cocatalyst, such as CuI, and a base, such as diethylamine, N,N-diisopropylethylamine, and preferably triethylamine. The reaction is usually carried out under anhydrous and anaerobic conditions. The reaction may be carried out in a solvent such as dioxane, N,N-dimethylformamide, toluene and preferably in tetrahydrofuran and heating at a temperature usually comprised between 60° C.-100° C.

The compounds of formula XI are commercial or may be easily obtained from commercial compounds using standard procedures.

Moreover, some compounds of formula I can be obtained from other compounds of formula I, by appropriate conversion reactions of functional groups, in one or more steps, using reactions that are well known in organic chemistry under standard experimental conditions.

As previously mentioned, the compounds of the present invention show potent histamine H$_4$ receptor antagonist activity. Therefore, the compounds of the invention are expected to be useful to treat diseases mediated by the H$_4$ receptor in mammals, including human beings.

Diseases that can be treated with the compounds of the invention include, among others, allergic, immunological or inflammatory diseases or pain.

Examples of allergic, immunological or inflammatory diseases that can be treated with the compounds of the invention include without limitation: respiratory diseases, such as asthma, allergic rhinitis and chronic obstructive pulmonary disease (COPD); ocular diseases, such as allergic rhinoconjunctivitis, dry eye and cataracts; skin diseases, such as dermatitis (e.g. atopic dermatitis), psoriasis, urticaria and pruritus; inflammatory bowel diseases, such as ulcerative colitis and Crohn's disease; rheumatoid arthritis; multiple sclerosis; cutaneous lupus; systemic lupus erythematosus; and transplant rejection.

Examples of pain conditions that can be treated with the compounds of the invention include, among others, inflammatory pain, inflammatory hyperalgesia, hyperalgesia, post-surgical pain, migraine, cancer pain, visceral pain, osteoarthritis pain and neuropathic pain.

In a preferred embodiment, the compounds of the invention are used for the treatment of an allergic, immunological or inflammatory disease. In a more preferred embodiment, the compounds of the invention are used for the treatment of an allergic, immunological or inflammatory disease selected from a respiratory disease, an ocular disease, a skin disease, an inflammatory bowel disease, rheumatoid arthritis, multiple sclerosis, cutaneous lupus, systemic lupus erythematosus, and transplant rejection. In a still more preferred embodiment, the allergic, immunological or inflammatory disease is selected from asthma, allergic rhinitis, chronic obstructive pulmonary disease (COPD), allergic rhinoconjunctivitis, dry eye, cataracts, dermatitis (e.g. atopic dermatitis), psoriasis, urticaria, pruritus, ulcerative colitis, Crohn's disease, rheumatoid arthritis, multiple sclerosis, cutaneous lupus, systemic lupus erythematosus and transplant rejection.

In another preferred embodiment, the compounds of the invention are used for the treatment of pain, preferably inflammatory pain, inflammatory hyperalgesia, hyperalgesia, post-surgical pain, migraine, cancer pain, visceral pain, osteoarthritis pain or neuropathic pain.

Assays to determine the ability of a compound to interact with the histamine H$_4$ receptor are well known in the art. For example, one can use a H$_4$ receptor binding assay such as the one explained in detail in example 29. Another useful assay is a GTP[$\gamma$-$^{35}$S] binding assay to membranes that express the H$_4$ receptor. Functional assays with H$_4$ receptor-expressing cells can also be used, for example in a system measuring any kind of cellular activity mediated by a second messenger associated with the H$_4$ receptor, such as intracellular cAMP levels or Ca$^{2+}$ mobilization. In this regard, a very useful functional assay that can be used to determine anti-H$_4$ receptor activity is the Gated Autofluorescence Forward Scatter assay (GAFS) in eosinophils, for example human eosinophils, as disclosed in detail in example 30; this assay is well know in the art (see for example the method disclosed in Buckland K F et al, 2003, cited above in the Background section, which is incorportated herein by reference). In vivo assays that can be used to test the activity of the compounds of the invention are also well known in the art (see for example the various literature references listed for in vivo animal models in the Background section, particularly those relating to in vivo models of peritonitis, pleurisy, allergic asthma, inflammatory bowel disease, atopic dermatitis, pruritus and pain, which are all incorportated herein by reference).

The selectivity profile of the compounds of the invention can be tested using standard histamine receptor binding assays using the various histamine receptors similarly to the one disclosed in example 29. In addition, to test the selectivity for other receptors or ion channels, displacement assays of the corresponding radioligands can be used following the standard procedures reported in the literature (see for example Cerep-Le Bois l'Evèque 2008 catalogue and the references cited therein). To test the selectivity for enzymes, determination of enzymatic activity by product formation from its substrate can be used.

For selecting active compounds, testing at 10 µM must result in an activity of more than 50% inhibition of H$_4$ receptor activity in the test provided in example 29. More preferably, compounds should exhibit more than 50% inhibition at 1 µM and still more preferably at 0.1 µM in this assay. Preferred compounds should also exhibit potent activity in the GAFS assay of example 30; preferably, compounds should exhibit more than 50% inhibition at 10 µM, more preferably at 1 µM and still more preferably at 0.1 µM in this assay.

Preferred compounds should exhibit selective affinity for the H$_4$ receptor over other receptors, particularly the H$_3$, muscarinic, adrenergic, dopamine and serotonine receptors.

The present invention also relates to a pharmaceutical composition comprising a compound of formula I (or a pharmaceutically acceptable salt or solvate thereof) and one or more pharmaceutically acceptable excipients. The excipients must be "acceptable" in the sense of being compatible with the other ingredients of the composition and not deleterious to the recipients thereof.

The compounds of the present invention can be administered in the form of any pharmaceutical formulation, the nature of which, as it is well known, will depend upon the nature of the active compound and its route of administration. Any route of administration may be used, for example oral, parenteral, nasal, ocular, topical and rectal administration.

Solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogenphosphate; binding agents such as for example starch, gelatin or povidone; disintegrants such as sodium carboxymethyl starch or sodium croscarmellose; and lubricating agents such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, in which the active compound is mixed with water or an oily medium, for example coconut oil, mineral oil or olive oil.

Powders and granulates for the preparation of oral suspensions by the addition of water can be obtained by mixing the active compound with dispersing or wetting agents; suspending agents and preservatives. Other excipients can also be added, for example sweetening, flavouring and colouring agents.

Liquid forms for oral administration include emulsions, solutions, suspensions, syrups and elixirs containing commonly-used inert diluents, such as purified water, ethanol, sorbitol, glycerol, polyethylene glycols (macrogols) and propylene glycol. Said compositions can also contain coadjuvants such as wetting, suspending, sweetening, flavouring agents, preservatives and buffers.

Injectable preparations, according to the present invention, for parenteral administration, comprise sterile solutions, suspensions or emulsions, in an aqueous or non-aqueous solvent such as propylene glycol, polyethylene glycol or vegetable oils. These compositions can also contain coadjuvants, such as wetting, emulsifying, dispersing agents and preservatives. They may be sterilized by any known method or prepared as sterile solid compositions which will be dissolved in water or any other sterile injectable medium immediately before use. It is also possible to start from sterile materials and keep them under these conditions throughout all the manufacturing process.

The compounds of the invention can also be formulated for their topical application for the treatment of pathologies occurring in zones or organs accessible through this route, such as eyes, skin and the intestinal tract. Formulations include creams, lotions, gels, powders, solutions and patches wherein the compound is dispersed or dissolved in suitable excipients.

For the nasal administration or for inhalation, the compound can be formulated as an aerosol, from which it can be conveniently released using suitable propellants.

The dosage and frequency of doses will depend upon the nature and severity of the disease to be treated, the age, the general condition and body weight of the patient, as well as the particular compound administered and the route of administration, among other factors. As an example, a suitable dosage range is from about 0.01 mg/Kg to about 100 mg/Kg per day, which can be administered as a single or divided doses.

The invention is illustrated with the following examples.

EXAMPLES

The following abbreviations are used in the examples:

AcN: acetonitrile
BINAP: 2,2'-bis(diphenylphosphino)-1,1'-binaphthyl
n-BuOH: 1-butanol
Conc: concentrate
DIEA: N,N-diisopropylethylamine
EtOAc: ethyl acetate
EtOH: ethanol
MeOH: methanol
Min: minutes
MS: mass spectrometry
NMP: 1-methyl-2-pyrrolidinone
$Pd_2(dba)_3$: tris(dibenzylideneacetone)dipalladium(0)
PyBOP: (benzotriazol-1-yloxy)tripyrrolidinophosphonium hexafluorophosphate
TEA: triethylamine
THF: tetrahydrofuran
$t_R$: retention time
LC-MS: liquid chromatography-mass spectrometry One of the following methods was used to determine the LC-MS spectrums:

Method 1: X-Terra MS C18 column 5 μm (100 mm×2.1 mm), temperature: 30° C., rate: 0.35 mL/min, eluent: A=AcN, B=$NH_4HCO_3$ 10 mM, gradient: 0 min A at 10%; 10 min A at 90%; 15 min A at 90%.

Method 2: Acquity HPLC BEH C18 1.7 μm (2.1×50 mm) column, temperature: 40° C., rate: 0.50 mL/min, eluent: A=AcN, B=$NH_4HCO_3$ 10 mM, gradient: 0 min A at 10%; 0.25 min A at 10%; 3.00 min A at 90%; 3.75 min A at 90%.

Reference Example 1 tert-Butyl methyl[(3R)-pyrrolidin-3-yl]carbamate (a) tert-Butyl [(3R)-1-benzylpyrrolidin-3-yl]methylcarbamate A solution of di-tert-butyl dicarbonate (11.6 g, 53.07 mmol) in 15 mL of $CH_2Cl_2$ was added to a solution of (3R)-1-benzyl-N-methylpyrrolidin-3-amine (10 g, 52.55 mmol) in 115 mL of $CH_2Cl_2$, cooled at 0° C. The resulting solution was stirred at room temperature for 18 hours. The solvent was evaporated and the crude product was chromatographed over silica gel using hexane/EtOAc mixtures of increasing polarity as eluent, providing 14.5 g of the desired compound (yield: 95%).

LC-MS (Method 1): $t_R$=9.55 min; m/z=291 (MH$^+$).

(b) Title compound

A solution of the compound obtained above (14.5 g, 50.14 mmol), Pd/C (10%, 50% in water) (3 g) and ammonium formate (12.7 g, 200.5 mmol) in a mixture of MeOH (390 mL) and water (45 mL) was heated under reflux for 5 hours. The reaction was filtered through Celite® and the filter aid was washed with EtOAc and MeOH. The solvent was evaporated to dryness, providing 10.6 g of the title compound in the form of an oil (yield: 100%).

$^1$H RMN (300 MHz, CDCl$_3$) δ: 1.38 (s, 9H), 1.72 (m, 1H), 1.96 (m, 1H), 2.53 (s, NH), 2.80 (s, 3H), 2.87 (m, 1H), 2.93 (m, 1H), 3.11 (m, 2H), 4.58 (m, 1H).

Reference Example 2 tert-Butyl azetidin-3-yl(methyl)carbamate (a) tert-Butyl [1-(diphenylmethyl)azetidin-3-yl]methylcarbamate Following a procedure similar to that described in section a) of reference example 1, but using 1-(diphenylmethyl)-N-methylazetidin-3-amine instead of (3R)-1-benzyl-N-methylpyrrolidin-3-amine, the desired compound was obtained (yield: 73%).

LC-MS (Method 1): $t_R$=10.14 min; m/z=353 (MH$^+$).

(b) Title Compound

A solution of the compound obtained above (6.18 g, 17.53 mmol) in 60 mL of MeOH and 15 mL of EtOAc was purged with argon. Pd/C (10%, 50% in water) (929 mg) was added and the solution was then purged again with argon and stirred in an H$_2$ atmosphere for 18 hours. The reaction was filtered through Celite® and the filter aid was washed with EtOAc and MeOH. The solvent was evaporated to dryness, providing 5.66 g of a mixture of the title compound together with one equivalent of diphenylmethane that was used as such in the following steps.

$^1$H RMN (300 MHz, CD$_3$OD) δ: 1.44 (s, 9H), 2.88 (s, 3H), 3.56 (m, 2H), 3.71 (m, 2H), 4.75 (m, 1H).

Reference Example 3

6-Chloro-2-isobutylpyrimidin-4-amine

Method A 2,6-Dichloropyrimidin-4-amine (0.75 g, 4.56 mmol), palladium acetate (51 mg, 0.23 mmol) and tri-tert-butylphosphine (0.45 mL of a 1 M solution in toluene, 0.45 mmol) were introduced in a flask and the system was purged three times with vacuum/argon cycles. A 2:1 THF-NMP mixture (24 mL) was then added and it was purged again three times with vacuum/argon. It was stirred for 10 minutes at room temperature and isobutylzinc bromide was added (13.7 mL of a 0.5 M solution in THF, 6.84 mmol). It was inertized again with vacuum/argon cycles and the reaction mixture was heated overnight at 100° C. The reaction crude was cooled to room temperature and filtered over Celite®, and the filter was washed with ethyl acetate. The filtrate was evaporated to dryness, the residue was diluted with ethyl acetate and the phases were separated. The organic phase was washed three times with water, it was dried over Na$_2$SO$_4$ and concentrated to dryness. The residue was purified by chromatography over silica gel using mixtures of hexane/EtOAc of increasing polarity as eluent, providing 0.69 g of the title compound as a 1:1 mixture of the two regioisomers (yield: 81% as the isomeric mixture, ca 40% for the intended isomer).

LC-MS (Method 2): $t_R$=1.64 min; m/z 186/188 (MH$^+$).

Method B

Reference example 31 (2 g, 12 mmol) was suspended in phosphorus oxychloride (11.1 mL, 120 mmol) and the mixture was heated to reflux for 10 h, the mixture becoming a solution. Solvent and phosphorus oxychloride were distilled off under vacuum. THF (36 mL) and 0.5 N HCl (36 mL) were added to the residue and the mixture heated to reflux for 2 h. The mixture was cooled down to room temperature and diluted with ethyl acetate. The phases were separated and the organic phase discarded. The acidic phase was washed again with ethyl acetate that was again discarded, and the pH of the aqueous phase was adjusted to basic (around 10) with conc ammonia. The mixture was cooled in a fridge overnight upon which a solid precipitated. The product was collected by filtration, washed with water and dried in a vacuum oven providing 1.36 g of the desired compound (yield 62%)

Reference Examples 4-5

The following compounds were obtained by following a procedure similar to that described in reference example 3 method A, but using suitable starting materials instead of isobutylzinc bromide:

| Ref Example | Name | Starting material | Method (LC-MS) | $t_R$ (min) | m/z (MH$^+$) |
|---|---|---|---|---|---|
| 4 | 6-Chloro-2-cyclohexylmethylpyrimidin-4-amine | Cyclohexylmethylzinc bromide | 2 | 2.15 | 226/228 |
| 5 | 6-Chloro-2-(4-fluorobenzyl)pyrimidin-4-amine | 4-Fluorobenzylzinc bromide | 2 | 1.85 | 238/240 |

Reference Example 6

2-Isobutylpyrimidine-4,6-diol

Sodium (0.75 g, 32.94 mmol) and ethanol (20 mL) were introduced in a flask. Once all the sodium had dissolved, 3-methylbutanimidamide hydrochloride (1.5 g, 10.98 mmol) and diethyl malonate (1.67 mL, 10.98 mmol) were added. It was stirred for 1 hour at room temperature and for 5 hours under reflux. The reaction crude was cooled at room temperature and concentrated to dryness. The solid obtained was dissolved in water and the pH was adjusted to 5 with acetic acid. The precipitate formed was filtered providing 1.5 g of the title compound (yield: 81%).

LC-MS (Method 2): $t_R$=0.32 min; m/z 169 (MH$^+$).

Reference Examples 7-11

The following compounds were obtained by following a procedure similar to that described in reference example 6, but using suitable starting materials instead of 3-methylbutanimidamide hydrochloride:

| Ref Example | Name | Starting material | Method (LC-MS) | $t_R$ (min) | m/z (MH$^+$) |
|---|---|---|---|---|---|
| 7 | 2-Cyclopropylpyrimidine-4,6-diol | Cyclopropanecarboximidamide hydrochloride | 2 | 0.29 | 153 |
| 8 | 2-tert-Butylpyrimidine-4,6-diol | Pivalimidamide hydrochloride | 2 | 0.32 | 169 |
| 9 | 2-Isopropylpyrimidine-4,6-diol | Isobutyrimidamide hydrochloride | 2 | 0.28 | 155 |
| 10 | 2-(Cyclopropylmethyl)pyrimidine-4,6-diol | Cyclopropylacetimidamide hydrochloride | 2 | 0.30 | 167 |
| 11 | 2-(Phenoxymethyl)pyrimidine-4,6-diol | 2-Phenoxyacetimidamide hydrochloride | 2 | 0.64 | 219 |

Reference Example 12

4,6-Dichloro-2-isobutylpyrimidine

Phosphorus oxychloride (12.5 mL, 134.28 mmol) was added to the compound obtained in reference example 6 (1.5 g, 8.95 mmol) and it was stirred for 6 hours under reflux. Then, the excess phosphorus oxychloride was distilled off. The resulting residue was diluted with ethyl acetate and saturated aqueous solution of NaHCO$_3$. The phases were separated and the aqueous phase was extracted three times with ethyl acetate. The combined organic phases were dried over Na$_2$SO$_4$ and it was concentrated to dryness providing 2 g of the title compound with quantitative yield.

LC-MS (Method 2): $t_R$=2.70 min; m/z

Reference Examples 13-17

The following compounds were obtained by following a procedure similar to that described in reference example 12, but using suitable starting materials:

Reference Example 18

4-[3-(tert-Butoxycarbonyl(methyl)amino)azetidin-1-yl]-6-chloro-2-isobutylpyrimidine The compound obtained in reference example 2 (3.23 g of the 1:1 mixture with diphenylmethane, 9.13 mmol) was added to a solution of reference example 12 (2 g, 8.95 mmol) and DIEA (2.33 mL, 13.43 mmol) in EtOH (20 mL) and the resulting mixture was heated under reflux for 6 hours. It was allowed to cool and the solvent was evaporated to dryness. The crude product obtained was purified by chromatography over silica gel using mixtures of hexane/EtOAc of increasing polarity as eluent, providing 2 g of the title compound (yield: 65%).

LC-MS (Method 2): $t_R$=2.84 min; m/z 355/357 (MH$^+$).

Reference Examples 19-27

The following compounds were obtained by following a procedure similar to that described in reference example 18, but using suitable starting materials:

| Ref Example | Name | Starting material | Method (LC-MS) | $t_R$ (min) | m/z (MH$^+$) |
|---|---|---|---|---|---|
| 13 | 2-Cyclopropyl-4,6-dichloropyrimidine | Ref Ex 7 | 2 | 2.44 | (*) |
| 14 | 2-tert-Butyl-4,6-dichloropyrimidine | Ref Ex 8 | 2 | 2.94 | (**) |
| 15 | 4,6-Dichloro-2-isopropylpyrimidine | Ref Ex 9 | 2 | 2.57 | (***) |
| 16 | 2-(Cyclopropylmethyl)-4,6-dichloropyrimidine | Ref Ex 10 | 2 | 2.81 | |
| 17 | 4,6-Dichloro-2-(phenoxymethyl)pyrimidine | Ref Ex 11 | 2 | 2.49 | 255/257/259 |

(*) $^1$H RMN (300 MHz, CDCl$_3$) δ (TMS): 1.16 (m, 2H), 1.26 (m, 2H), 2.24 (m, 1H), 6.84 (s, 1H).

(**) $^1$H RMN (300 MHz, CDCl$_3$) δ (TMS): 1.44 (s, 9H) 6.40 (s, 1H).

(***) $^1$H RMN (300 MHz, CDCl$_3$) δ (TMS): 1.35 (d, J = 4.8 Hz, 6H), 3.2 (m, 1H), 7.28 (s, 1H).

| Ref Example | Name | Starting material | Method (LC-MS) | $t_R$ (min) | m/z (MH$^+$) |
|---|---|---|---|---|---|
| 19 | 4-[3-(tert-Butoxycarbonyl(methyl)amino)azetidin-1-yl]-6-chloro-2-cyclopropylpyrimidine | Ref Ex 13 and Ref Ex 2 | 2 | 2.71 | 339/341 |
| 20 | 4-[3-(tert-Butoxycarbonyl(methyl)amino)azetidin-1-yl]-2-tert-butyl-6-chloropyrimidine | Ref Ex 14 and Ref Ex 2 | 2 | 3.24 | 355/357 |
| 21 | 4-[3-(tert-Butoxycarbonyl(methyl)amino)azetidin-1-yl]-6-chloro-2-isopropylpyrimidine | Ref Ex 15 and Ref Ex 2 | 2 | 2.82 | 341/343 |
| 22 | 4-[3-(tert-Butoxycarbonyl(methyl)amino)azetidin-1-yl]-6-chloro-2-(cyclopropylmethyl)pyrimidine | Ref Ex 16 and Ref Ex 2 | 2 | 2.93 | 353/355 |
| 23 | 4-[3-(tert-Butoxycarbonyl(methyl)amino)azetidin-1-yl]-6-chloro-2-(phenoxymethyl)pyrimidine | Ref Ex 17 and Ref Ex 2 | 2 | 2.75 | 405/407 |
| 24 | 4-[(3R)-3-(tert-Butoxycarbonyl(methyl)amino)pyrrolidin-1-yl]-6-chloro-2-cyclopropylpyrimidine | Ref Ex 13 and Ref Ex 1 | 2 | 2.85 | 353/355 |
| 25 | 4-[(3R)-3-(tert-Butoxycarbonyl(methyl)amino)pyrrolidin-1-yl]-2-tert-butyl-6-chloropyrimidine | Ref Ex 14 and Ref Ex 1 | 2 | 3.34 | 369/371 |
| 26 | 4-[(3R)-3-(tert-Butoxycarbonyl(methyl)amino)pyrrolidin-1-yl]-6-chloro-2-isopropylpyrimidine | Ref Ex 15 and Ref Ex 1 | 2 | 2.99 | 355/357 |
| 27 | 4-[(3R)-3-(tert-Butoxycarbonyl(methyl)amino)pyrrolidin-1-yl]-6-chloro-2-(phenoxymethyl)pyrimidine | Ref Ex 17 and Ref Ex 1 | 2 | 2.88 | 419/421 |

Reference Example 28

2-(2-Cyclopentylethynyl)-6-chloropyrimidin-4-amine 2,6-Dichloropyrimidin-4-amine (0.2 g, 1.22 mmol), tetrakis(triphenylphosphine)palladium(0) (42 mg, 0.043 mmol) and copper iodide (14 mg, 0.07 mmol) were introduced in a flask. A mixture of THF-triethylamine 2:3 (5 mL) was added and the system was inertized 3 times with vacuum/argon cycles. Finally, cyclopentyl acetylene (0.16 mL, 1.34 mmol) was added and the resulting mixture was heated at 100° C. overnight. The reaction crude was cooled at room temperature and filtered over Celite®. The solvent was evaporated to dryness and the residue was purified by chromatography over silica gel using mixtures of hexane/EtOAc of increasing polarity as eluent, providing 0.15 g of the title compound, impurified with its regioisomer.

LC-MS (Method 2): $t_R$=1.98 min; m/z=222/224 (MH$^+$).

Reference Example 29

2-(2-Cyclopentylethynyl)-6-((3R)-3-(methylamino)pyrrolidin-1-yl)pyrimidin-4-amine (a) tert-Butyl (R)-1-(4-amino-2-(2-cyclopentylethynyl)pyrimidin-6-yl)pyrrolidin-3-yl(methyl)carbamate The compound obtained in reference example 1 (0.16 g, 0.8 mmol) was added to a mixture of the compound obtained in reference example 28 (0.15 g as a mixture of regioisomers, 0.67 mmol) and DIEA (0.13 g, 1.0 mmol) in n-BuOH (2 mL) and the resulting mixture was heated overnight in a sealed tube at 100° C. It was allowed to cool and the solvent was evaporated to dryness. The crude product obtained was purified by chromatography over silica gel using mixtures of hexane/EtOAc of increasing polarity as eluent, providing 85.5 mg of the title compound (yield: 18% from 2,6-dichloropyrimidin-4-amine).

LC-MS (Method 2): $t_R$=2.65 min; m/z=386 (MH$^+$).

(b) Title Compound

Trifluoroacetic acid (0.5 mL) was added to a solution of the compound obtained in section a) (85.5 mg, 0.22 mmol) in anhydrous dichloromethane (9.5 mL) cooled at 0° C., and the resulting mixture was stirred at room temperature for 3 hours. The solvent was evaporated to dryness and the crude product was dissolved in EtOAc and water. The phases were separated and the organic phase was discarded. The pH of the aqueous phase was adjusted to 9 with 1 N NaOH and extracted three times with chloroform. The combined organic phases were dried over Na$_2$SO$_4$ and it was concentrated to dryness providing 47.3 mg of the intended compound (yield: 75%).

LC-MS (Method 2): $t_R$=1.64 min; m/z=286 (MH$^+$).

Reference Example 30 tert-Butyl 3-methylazetidin-3-yl(methyl)carbamate (a) tert-Butyl [1-(diphenylmethyl)-3-methylazetidin-3-yl]methylcarbamate Following a procedure similar to that described in section a) of reference example 1, but using 1-(diphenylmethyl)-N,3-dimethylazetidin-3-amine instead of (3R)-1-benzyl-N-methylpyrrolidin-3-amine, the desired compound was obtained with quantitative yield.

$^1$H NMR (300 MHz, CDCl$_3$) δ: 1.53 (s, 12H), 2.59 (s, 3H), 2.89 (m, 2H), 3.16 (m, 2H), 4.30 (s, 1H), 7.17 (m, 1H), 7.26 (m, 2H), 7.42 (m, 1H).

(b) Title Compound

A solution of the compound obtained in section a) (6.06 g, 16.5 mmol) in 60 mL of MeOH and 15 mL of EtOAc was purged with argon. Pd/C (10%) (814 mg) was added and the mixture was then purged again with argon and stirred overnight in an H$_2$ atmosphere. The reaction was filtered through Celite® and the filter cake was washed with EtOAc and MeOH. The solvent was evaporated to dryness, providing 4.55 g of a mixture of the title compound together with one equivalent of diphenylmethane that was used as such in the following steps.

$^1$H NMR (300 MHz, CDCl$_3$) δ: 1.45 (s, 12H), 2.67 (s, 3H), 3.28 (m, 1H), 3.61 (m, 1H), 3.87 (m, 1H), 4.00 (m, 1H)

Reference Example 31

6-Amino-2-isobutylpyrimidin-4-ol

Sodium ethoxide (210 mL of a 21% solution in ethanol, 563 mmol) was diluted with absolute ethanol (290 mL). To the sodium ethoxide solution were then sequentially added 3-methylbutanimidamide acetate (45 g, 281 mmol) and ethyl 3-ethoxy-3-iminopropionate hydrochloride (59 g 85% purity, 256 mmol) and the mixture was heated to reflux overnight. The mixture was cooled down, solvent was stripped off and the residue was diluted with water (100 mL). pH was adjusted to 6-7 with 2 N HCl and the slurry was heated to reflux. Water (350 mL) was added although total dissolution of the solids was not achieved. The solids were collected by filtration and dried under vacuum to yield 18.6 g of the title compound. Upon cooling additional product precipitated, that was isolated by filtration and dried under vacuum to yield additional 8.18 g of product. The combined solids accounted for a total of 26.8 g (yield: 62%).

LC-MS (Method 2): $t_R$=0.84 min; m/z 168 (MH$^+$).

Reference Examples 32-34

The following compounds were obtained by following a procedure similar to that described in reference example 31, but using suitable starting materials instead of 3-methylbutanimidamide:

| Ref Example | Name | Starting material | Method (LC-MS) | $t_R$ (min) | m/z (MH$^+$) |
|---|---|---|---|---|---|
| 32 | 6-Amino-2-(2,2-dimethylpropyl)pyrimidin-4-ol | 3,3-dimethylbutanimidamide acetate | 2 | 1.06 | 182 |
| 33 | 6-Amino-2-cyclobutylpyrimidin-4-ol | Cyclobutanecarboxamidine acetate | 2 | 0.76 | 166 |
| 34 | 6-Amino-2-cyclopentylpyrimidin-4-ol | Cyclopentanecarboxamidine acetate | 2 | 1.01 | 180 |

Example 1

2-Isobutyl-6-((3R)-3-(methylamino)pyrrolidin-1-yl)pyrimidin-4-amine

The compound obtained in reference example 1 (144 mg, 0.72 mmol) was added to a solution of reference example 3 (89 mg as an approx 50% mixture of the two regioisomers, 0.48 mmol equivalents to 0.24 mmol of the intended regioisomer) and DIEA (0.25 mL, 1.44 mmol) in n-BuOH (6 mL), and the resulting mixture was heated overnight in a sealed tube at 100° C. Additional reference example 1 (96 mg, 0.48 mmol) and DIEA (0.25 mL) were added and it was heated at 100° C. for one more day. It was allowed to cool and the solvent was evaporated to dryness. The crude product obtained was purified by preparative HPLC-MS (column X-Terra PREP MS C18 5 μm (100 mm×19 mm), rate: 20 mL/min, eluent: A=AcN, B=NH$_4$HCO$_3$ 75 mM, gradient: 0 min A at 25%; 1 min A at 25%; 11 min A at 90%; 12 min A at 90%) and the fractions containing the product were evaporated to dryness, providing 26.9 mg of the Boc-protected intermediate (yield: 32%), HCl (4 M solution in 1,4-dioxane, 1.5 mL) and MeOH (1 mL) were added to this intermediate, and the mixture was stirred at room temperature for 2 hours. The solvent was evaporated to dryness. The residue was dissolved in water, 1 N NaOH solution was added until basic pH and it was extracted three times with chloroform. The combined organic phases were dried over anhydrous Na$_2$SO$_4$ and it was concentrated to dryness. The crude product obtained was purified by preparative HPLC-MS (column X-Terra PREP MS C18 5 μm (100 mm×19 mm), rate: 20 mL/min, eluent: A=AcN, B=NH$_4$HCO$_3$ 75 mM, gradient: 0 min A at 10%; 1 min A at 10%; 8 min A at 90%) and the fractions containing the product were evaporated to dryness, providing 5.2 mg of the title compound (yield: 27%).

LC-MS (Method 2): $t_R$=1.20 min; m/z 250 (MH$^+$).

Examples 2-3

The following compounds were obtained by following a procedure similar to that described in example 1, but using suitable starting materials:

| Example | Name | Starting material | Method (LC-MS) | $t_R$ (min) | m/z (MH$^+$) |
|---|---|---|---|---|---|
| 2 | 2-Cyclohexylmethyl-6-((3R)-3-(methylamino)pyrrolidin-1-yl)pyrimidin-4-amine | Ref Ex 4 and Ref Ex 1 | 2 | 1.65 | 290 |
| 3 | 2-(4-Fluorobenzyl)-6-(3-(methylamino)azetidin-1-yl)pyrimidin-4-amine | Ref Ex 5 and Ref Ex 2 | 2 | 1.38 | 288 |

Example 4

2-Isobutyl-6-(3-(methylamino)azetidin-1-yl)pyrimidin-4-amine

Method A

Reference compound 18 (2 g, 6.0 mmol), benzophenoneimine (1.1 mL, 6.60 mmol), sodium tert-butoxide (0.86 g, 9.0 mmol), racemic BINAP (0.22 g, 0.36 mmol) and toluene (60 mL) were arranged in a schlenk tube. The system was purged three times with vacuum/argon cycles. Pd$_2$(dba)$_3$ (0.11 g, 0.12 mmol) was then added and it was purged again three times with vacuum/argon. The reaction mixture was heated at 85° C. overnight. The reaction crude was cooled at room temperature and filtered over Celite®, and the filter cake was washed with ethyl acetate. The filtrate was evaporated to dryness. The residue was dissolved in THF (127 mL), 3N HCl (127 mL) was then added and it was stirred for 3 hours at room temperature. It was evaporated to dryness. The crude product was dissolved in water and ethyl acetate, phases were separated and the organic phase was discarded. 0.5 N NaOH was then added to the acidic aqueous phase until basic pH. The aqueous phase was extracted with EtOAc three times. The combined organic phases were dried over Na$_2$SO$_4$ and it was concentrated to dryness. The residue was purified by chromatography over silica gel using mixtures of hexane/EtOAc of increasing polarity as eluent, providing 0.67 g of the title compound (yield: 23%)

LC-MS (Method 2): $t_R$=1.15 min; m/z 236 (MH$^+$).

Method B

Reference example 3 (163 mg, 0.88 mmol), reference example 2 (500 mg of a 1:1 mixture with diphenylmethane, 1.4 mmol) and N,N-diisopropylethylamine (245 μL, 1.4 mmol) were added to ethanol (2 mL), and the mixture stirred under reflux (oil bath temperature set at 100° C.) overnight. Solvent was distilled off and the residue diluted with 0.2 N NaHCO$_3$ and ethyl acetate. Phases were separated and the aqueous phase was extracted twice more with ethyl acetate. The combined organic phases were dried over Na$_2$SO$_4$ and it was concentrated to dryness providing the Boc-protected precursor. This crude product was dissolved in methanol (6 mL) and 4 M HCl in 1,4-dioxane (6 mL) was added. The mixture was stirred at room temperature for 2 h, and then evaporated to dryness. The residue was dissolved in water and the acidic phase was washed twice with ethyl acetate, that was discarded. pH of the aqueous phase was then adjusted to basic (>9) and the product was extracted three times with ethyl acetate. The combined organic phases were dried over Na$_2$SO$_4$ and the solvent evaporated to dryness. The crude product obtained was purified by chromatography over silica gel using mixtures of EtOAc/MeOH/NH$_3$ $_{conc}$ of increasing polarity as eluent, providing 136 mg of the title compound (yield: 36%).

Examples 5-13

The following compounds were obtained by following a procedure similar to that described in example 4 Method A, but using suitable starting materials:

| Example | Name | Starting material | Method (LC-MS) | $t_R$ (min) | m/z (MH$^+$) |
|---|---|---|---|---|---|
| 5 | 2-Cyclopropyl-6-(3-(methylamino)azetidin-1-yl)pyrimidin-4-amine | Ref Ex 19 | 2 | 1.03 | 220 |
| 6 | 2-tert-Butyl-6-(3-(methylamino)azetidin-1-yl)pyrimidin-4-amine | Ref Ex 20 | 2 | 1.48 | 236 |
| 7 | 2-Isopropyl-6-(3-(methylamino)azetidin-1-yl)pyrimidin-4-amine | Ref Ex 21 | 2 | 1.08 | 222 |
| 8 | 2-(Cyclopropylmethyl)-6-(3-(methylamino)azetidin-1-yl)pyrimidin-4-amine | Ref Ex 22 | 2 | 1.22 | 234 |
| 9 | 6-(3-(methylamino)azetidin-1-yl)-2-(phenoxymethyl)pyrimidin-4-amine | Ref Ex 23 | 2 | 1.33 | 286 |
| 10 | 2-Cyclopropyl-6-((3R)-3-(methylamino)pyrrolidin-1-yl)pyrimidin-4-amine | Ref Ex 24 | 2 | 1.02 | 234 |
| 11 | 2-tert-Butyl-6-((3R)-3-(methylamino)pyrrolidin-1-yl)pyrimidin-4-amine | Ref Ex 25 | 2 | 1.55 | 250 |

-continued

| Example | Name | Starting material | Method (LC-MS) | $t_R$ (min) | m/z (MH$^+$) |
|---|---|---|---|---|---|
| 12 | 2-Isopropyl-6-((3R)-3-(methylamino)pyrrolidin-1-yl)pyrimidin-4-amine | Ref Ex 26 | 2 | 1.15 | 236 |
| 13 | 6-((3R)-3-(methylamino)pyrrolidin-1-yl)-2-(phenoxymethyl)pyrimidin-4-amine | Ref Ex 27 | 2 | 1.36 | 300 |

Example 14

6-(3-Aminoazetidin-1-yl)-2-isobutylpyrimidin-4-amine

Following a procedure similar to that described in Method B of example 4, but using tert-butyl azetidin-3-ylcarbamate instead of reference example 2, the desired compound was obtained.

LC-MS (Method 2): $t_R$=0.97 min; m/z 222 (MH$^+$).

Example 15

2-Isobutyl-6-(3-methyl-3-(methylamino)azetidin-1-yl)pyrimidin-4-amine a) tert-Butyl 1-(6-amino-2-isobutylpyrimidin-4-yl)-3-methylazetidin-3-yl(methyl)carbamate The compound obtained in reference example 31 (0.15 g, 0.90 mmol), the amine obtained in reference example 30 (0.57 g of a 1:1 mixture with diphenylmethane, equivalent to 0.29 g 100%, 1.4 mmol) and PyBOP (0.52 g, 0.99 mmol) in a mixture of TEA (6 mL), acetonitrile (6 mL) and 1,4-dioxane (6 mL) were heated at 90° C. for 2 days. The reaction mixture was concentrated to dryness. The crude product obtained was purified by chromatography over silica gel using mixtures of hexane/EtOAc of increasing polarity as eluent, providing 229 mg of the desired compound (yield: 73%)

LC-MS (Method 2): $t_R$=2.15 min; m/z 350 (MH$^+$).

b) Title Compound

The compound obtained in section a) was stirred in a mixture of 1,4-dioxane (5 mL) and HCl (4 M solution in 1,4-dioxane, 5 mL) at room temperature for 2 hours. The solvent was evaporated to dryness. The residue was dissolved in water and washed twice with EtOAc, that was discarded. 1 N NaOH solution was added to the acidic aqueous phase until basic pH and it was extracted twice with EtOAc. The combined organic phases were dried over anhydrous Na$_2$SO$_4$ and it was concentrated to dryness. The crude product obtained was purified by chromatography over silica gel using mixtures of EtOAc/MeOH/NH$_3\ conc$ of increasing polarity as eluent, providing 49 mg of the title compound (yield: 30%).

LC-MS (Method 2): $t_R$=1.22 min; m/z 250 (MH$^+$).

Examples 16-22

The following compounds were obtained by following a procedure similar to that described in example 15, but using suitable starting materials:

| Example | Name | Starting material | Method (LC-MS) | $t_R$ (min) | m/z (MH$^+$) |
|---|---|---|---|---|---|
| 16 | 6-((3R)-3-aminopyrrolidin-1-yl)-2-isobutylpyrimidin-4-amine | Ref Ex 31 and tert-butyl [(3R)-pyrrolidin-3-yl]carbamate | 2 | 1.08 | 236 |
| 17 | 2-Cyclobutyl-6-(3-(methylamino)azetidin-1-yl)pyrimidin-4-amine | Ref Ex 33 and ref ex 2 | 2 | 1.14 | 234 |
| 18 | 2-Cyclobutyl-6-((3R)-3-(methylamino)pyrrolidin-1-yl)pyrimidin-4-amine | Ref Ex 33 and ref ex 1 | 2 | 1.20 | 248 |
| 19 | 2-Cyclopentyl-6-(3-(methylamino)azetidin-1-yl)pyrimidin-4-amine | Ref Ex 34 and ref ex 2 | 2 | 1.32 | 248 |
| 20 | 2-Cyclopentyl-6-((3R)-3-(methylamino)pyrrolidin-1-yl)pyrimidin-4-amine | Ref Ex 34 and ref ex 1 | 2 | 1.38 | 262 |
| 21 | 2-(2,2-Dimethylpropyl)-6-(3-(methylamino)azetidin-1-yl)pyrimidin-4-amine | Ref Ex 32 and ref ex 2 | 2 | 1.31 | 250 |
| 22 | 2-(2,2-Dimethylpropyl)-6-((3R)-3-(methylamino)pyrrolidin-1-yl)pyrimidin-4-amine | Ref Ex 32 and ref ex 1 | 2 | 1.36 | 264 |

Example 23

2-(2-Cyclopentylethyl)-6-((3R)-3-(methylamino)pyrrolidin-1-yl)pyrimidin-4-amine A solution of reference example 29 (44 mg, 0.15 mmol) in 1.8 mL of MeOH was purged with argon. Pd/C (5%, 50% in water) (14 mg) was added and the mixture was then purged again with argon and stirred overnight in an $H_2$ atmosphere. The reaction was filtered through Celite® and the filter cake was washed with MeOH. The solvent was evaporated to dryness and the crude product obtained was purified by Preparative HPLC-MS (C18 X-Bridge PREP Column OBD 5 μm (50 mm×19 mm), rate: 19 mL/min with an ACD (At Column Dilution) of AcN at 1 mL/min, eluent: A=AcN, B=$NH_4HCO_3$ 75 mM, gradient: 0 min A at 5%; 3 min A at 5%; 10 min A at 85%). The fractions containing the product were evaporated to dryness providing 17.4 mg of the intended compound (yield: 39%).

LC-MS (Method 2): $t_R$=1.86 min; m/z 290 (MH+).

Examples 24-28

Following similar procedures to the ones described above, but starting from appropriate starting materials, the following additional compounds can be made:

| Example | Name |
|---|---|
| 24 | 2-Cyclohexylmethyl-6-(3-(methylamino)azetidin-1-yl)pyrimidin-4-amine |
| 25 | 2-Cyclopropylmethyl-6-((3R)-3-(methylamino)pyrrolidin-1-yl)pyrimidin-4-amine |
| 26 | 2-Cyclohexyl-6-(3-(methylamino)azetidin-1-yl)pyrimidin-4-amine |
| 27 | 2-Cyclohexyl-6-((3R)-3-(methylamino)pyrrolidin-1-yl)pyrimidin-4-amine |
| 28 | 2-(4-Fluorobenzyl)-6-((3R)-3-(methylamino)pyrrolidin-1-yl)pyrimidin-4-amine |

Example 29

Competitive Binding Assay of [³H]-histamine to the Human Histamine $H_4$ Receptor To perform the binding assay, membrane extracts prepared from a stable CHO recombinant cell line expressing the human histamine $H_4$ receptor (Euroscreen/Perkin-Elmer) were used.

The compounds to be tested were incubated at the desired concentration in duplicate with 10 nM [³H]-histamine and 15 μg membrane extract in a total volume of 250 μL of 50 mM Tris-HCl, pH 7.4, 1.25 mM EDTA for 60 minutes at 25° C. Non-specific binding was defined in the presence of 100 μM of unlabelled histamine. The reaction was stopped by filtration using a vacuum collector (Multiscreen Millipore) in 96-well plates (MultiScreen HTS Millipore) that had been previously soaked in 0.5% polyethylenimine for 2 hours at 0° C. The plates were subsequently washed with 50 mM Tris (pH 7.4), 1.25 mM EDTA at 0° C., and the filters were dried for 1 hour at 50-60° C., before adding the scintillation liquid in order to determine bound radioactivity by means of a beta-plate scintillation counter.

The compounds of examples 1 to 7 and 9 to 23 were assayed in this test and exhibited more than 50% inhibition of histamine binding to human histamine $H_4$ receptor at 10 μM. Moreover, the compounds of examples 1 to 7, 10, 11, 12 and 14 to 22 gave more than 50% inhibition at a concentration of 1 μM.

Example 30

Histamine-induced Shape Change Assay (Gated Autofluorescence Forward Scatter Assay, GAFS) in Human Eosinophils In this assay the shape change induced by histamine in human eosinophils is determined by flow cytometry, detected as an increase in the size of the cells (forward scatter, FSC).

Polymorphonuclear leucocytes (PMNL, fraction containing neutrophils and eosinophils) were prepared from whole blood of human healthy volunteers. Briefly, erythrocytes were separated by sedimentation in 1.2% Dextran (SIGMA), and the leucocyte-rich fraction (PMNL) was isolated from the top layer by centrifugation at 450 g for 20 min in the presence of Ficoll-Paque® (Biochrom). PMNLs were resuspended in PBS buffer at a concentration of $1.1 \times 10^6$ cells/ml/tube and were pretreated with different concentrations of test compounds (dissolved in PBS) for 30 min at 37° C. and then stimulated with 300 nM histamine (Fluka) for 5 min. Finally, paraformaldehyde (1% final concentration in PBS) was added to terminate the reaction and maintain cell shape. Cell shape change was analyzed by flow cytometry (FACS Calibur, BD Biosystems). Eosinophils in PMNL were gated based on their higher autofluorescence relative to that of neutrophils (fluorescence channel FL2). Cell shape change was monitored in forward scatter signals (FSC). Results are expressed as percentage inhibition of shape change induced by histamine for each concentration of test compound.

The compounds of examples 1 to 4, 11, 12, 15 and 17 to 22 were assayed in this test and produced more than 50% inhibition of histamine-induced human eosinophil shape change at 1 μM.

The invention claimed is:

1. A compound of formula (I):

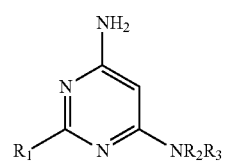

(I)

or a pharmaceutically acceptable salt thereof, wherein:

$R_1$ is selected from:
  (1) $C_{1-8}$ alkyl;
  (2) $C_{3-8}$ cycloalkyl-$C_{0-6}$ alkyl;
  (3) aryl-$C_{1-6}$ alkyl; wherein in groups (1) to (3) any alkyl group may be optionally substituted with one or more halogen groups and the $C_{3-8}$ cycloalkyl group may be optionally substituted with one or more substituents selected from $C_{1-4}$ alkyl, halogen and aryl;

(4) a group of formula (i)

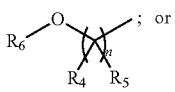

(i)

(5) a group of formula (ii)

(ii)

$R_2$ and $R_3$ form, together with the N atom to which they are bound, a saturated heterocyclic group that can be 4- to 7-membered monocyclic, 7- to 8-membered bridged bicyclic, or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group; or $R_2$ is selected from H and $C_{1-4}$ alkyl, and $R_3$ is selected from azetidinyl, pyrrolidinyl, piperidinyl and azepanyl, each of which may be optionally substituted with one or more $C_{1-4}$ alkyl groups;

$R_a$ is selected from H and $C_{1-4}$ alkyl;

$R_b$ is selected from H and $C_{1-4}$ alkyl;

or $R_a$ and $R_b$ form, together with the N atom to which they are bound, an azetidinyl, pyrrolidinyl, piperidinyl or azepanyl group, that may be optionally substituted with one or more $C_{1-4}$ alkyl groups;

$R_4$ and $R_5$ are each independently selected from H and $C_{1-4}$ alkyl, and additionally one of the $R_4$ or $R_5$ groups may be selected from aryl or $C_{3-6}$ cycloalkyl-$C_{0-6}$ alkyl, and additionally two $R_4$ and $R_5$ groups on a same C atom may be bound together forming with said C atom a $C_{3-8}$ cycloalkyl group;

$R_6$ is a group selected from $C_{1-8}$ alkyl, $C_{3-8}$ cycloalkyl-$C_{0-6}$ alkyl and aryl-$C_{0-4}$ alkyl, wherein any of said alkyl groups may be optionally substituted with one or more halogen groups and said $C_{3-8}$ cycloalkyl group may be optionally substituted with one or more substituents independently selected from $C_{1-4}$ alkyl, halogen and aryl;

$R_7$ is a saturated monocyclic 4- to 7-membered heterocyclic ring containing one O atom and not containing any other additional heteroatoms, wherein said ring may be bound to the rest of the molecule through any available C atom, and wherein $R_7$ may be optionally substituted with one or more groups independently selected from $C_{1-4}$ alkyl and halogen;

n is 1, 2 or 3;

p is 0, 1 or 2; and aryl is a phenyl group optionally substituted with one or more groups independently selected from $C_{1-4}$ alkyl, halogen, $C_{1-4}$ alkoxy, $C_{1-4}$ haloalkyl, $C_{1-4}$ haloalkoxy, cyano and amino.

2. A compound according to claim 1, or a pharmaceutically acceptable salt thereof, wherein $R_1$ is (1) $C_{4-6}$ alkyl; (2) $C_{3-8}$ cycloalkyl-$C_{0-1}$ alkyl; or (3) aryl-$C_{1-2}$ alkyl.

3. A compound according to claim 1, or a pharmaceutically acceptable salt thereof, wherein $R_1$ is a $C_{3-8}$ cycloalkyl-$C_{0-6}$ alkyl, wherein the alkyl group may be optionally substituted with one or more halogen groups and the $C_{3-8}$ cycloalkyl group may be optionally substituted with one or more substituents independently selected from $C_{1-4}$ alkyl, halogen and aryl.

4. A compound according to claim 1, or a pharmaceutically acceptable salt thereof, wherein $R_1$ is selected from a $C_{3-8}$ cycloalkyl optionally substituted with one or more substituents independently selected from $C_{1-4}$ alkyl, halogen and aryl.

5. A compound according to claim 4, or a pharmaceutically acceptable salt thereof, wherein $R_1$ is selected from cyclobutyl, cyclopentyl and cyclohexyl.

6. A compound according to claim 1, or a pharmaceutically acceptable salt thereof, wherein $R_1$ is $C_{3-8}$ cycloalkyl-$C_1$ alkyl.

7. A compound according to claim 6, or a pharmaceutically acceptable salt thereof, wherein $R_1$ is cyclopropylmethyl.

8. A compound according to claim 6, or a pharmaceutically acceptable salt thereof, wherein $R_1$ is cyclohexylmethyl.

9. A compound according to claim 1, or a pharmaceutically acceptable salt thereof, wherein $R_1$ is $C_{1-8}$ alkyl or $C_{3-6}$ cycloalkyl-$C_{0-6}$ alkyl, wherein the alkyl group may be optionally substituted with one or more halogen groups and the $C_{3-8}$ cycloalkyl group may be optionally substituted with one or more substituents independently selected from $C_{1-4}$ alkyl, halogen and aryl.

10. A compound according to claim 9, or a pharmaceutically acceptable salt thereof, wherein $R_1$ is $C_{1-8}$ alkyl or $C_{3-6}$ cycloalkyl-$C_{0-6}$ alkyl.

11. A compound according to claim 10, or a pharmaceutically acceptable salt thereof, wherein $R_1$ is $C_{4-6}$ alkyl or $C_{3-8}$ cycloalkyl-$C_{0-1}$ alkyl.

12. A compound according to claim 11, or a pharmaceutically acceptable salt thereof, wherein $R_1$ is selected from isobutyl, 2,2-dimethylpropyl, cyclobutyl, cyclopentyl, cyclohexyl, cyclohexylmethyl and cyclopropylmethyl.

13. A compound according to claim 1, or a pharmaceutically acceptable salt thereof, wherein $R_1$ is a $C_{1-6}$ alkyl optionally substituted with one or more halogen groups.

14. A compound according to claim 13, or a pharmaceutically acceptable salt thereof, wherein $R_1$ is $C_{4-6}$ alkyl.

15. A compound according to claim 14, or a pharmaceutically acceptable salt thereof, wherein $R_1$ is selected from isobutyl and 2,2-dimethylpropyl.

16. A compound according to claim 15, or a pharmaceutically acceptable salt thereof, wherein $R_1$ is isobutyl.

17. A compound according to claim 15, or a pharmaceutically acceptable salt thereof, wherein $R_1$ is 2,2-dimethylpropyl.

18. A compound according to claim 1, or a pharmaceutically acceptable salt thereof, wherein $R_2$ and $R_3$ form, together with the N atom to which they are bound, a saturated heterocyclic group that can be 4- to 7-membered monocyclic, 7- to 8-membered bridged bicyclic, or 8- to 12-membered fused bicyclic, wherein said heterocyclic group can contain up to two N atoms and does not contain any other heteroatoms, and can be optionally substituted with one or more substituents independently selected from $C_{1-4}$ alkyl and $NR_aR_b$, provided that the heterocyclic group either contains 2 N atoms and is not substituted with an $NR_aR_b$ group, or contains 1 N atom and is substituted with one $NR_aR_b$ group.

19. A compound according to claim 18, or a pharmaceutically acceptable salt thereof, wherein $R_2$ and $R_3$ form, together with the N atom to which they are bound, a saturated heterocyclic group selected from:

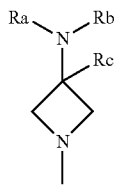

(a)

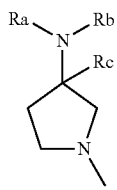

(b)

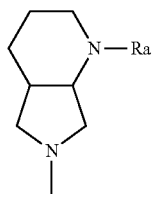

(c)

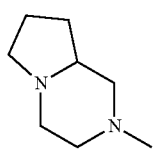

(d)

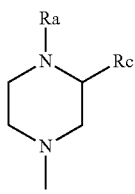

(e)

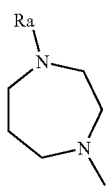

(f)

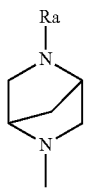

(g)

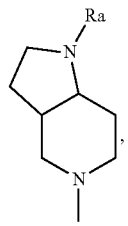

(h)

wherein $R_c$ is selected from H or $C_{1-4}$ alkyl.

20. A compound according to claim 19, or a pharmaceutically acceptable salt thereof, wherein $R_2$ and $R_3$ form, together with the N atom to which they are bound, a saturated heterocyclic group selected from (a) or (b).

21. A compound according to claim 20, or a pharmaceutically acceptable salt thereof, wherein $R_c$ is H.

22. A compound according to claim 19, or a pharmaceutically acceptable salt thereof, wherein $R_2$ and $R_3$ form, together with the N atom to which they are bound, a saturated heterocyclic group of formula (a).

23. A compound according to claim 22, or a pharmaceutically acceptable salt thereof, wherein $R_c$ is H.

24. A compound according to claim 19, or a pharmaceutically acceptable salt thereof, wherein $R_a$ and $R_b$ are each independently selected from H and $C_{1-4}$ alkyl.

25. A compound according to claim 24, or a pharmaceutically acceptable salt thereof, wherein $R_a$ and $R_b$ are each independently selected from H and methyl.

26. A compound according to claim 25, or a pharmaceutically acceptable salt thereof, wherein $R_a$ is H and $R_b$ is methyl.

27. A compound according to claim 19, or a pharmaceutically acceptable salt thereof, wherein $R_1$ is selected from $C_{4-6}$ alkyl or $C_{3-8}$ cycloalkyl-$C_{0-1}$ alkyl and $R_2$ and $R_3$ form, together with the N atom to which they are bound, a saturated heterocyclic group selected from (a) and (b).

28. A compound according to claim 27, or a pharmaceutically acceptable salt thereof, wherein $R_1$ is $C_{4-6}$ alkyl, $R_a$ and $R_b$ are each independently selected from H and methyl, and $R_c$ is H.

29. A compound according to claim 27, or a pharmaceutically acceptable salt thereof, wherein $R_2$ and $R_3$ form, together with the N atom to which they are bound, a saturated heterocyclic group of formula (a).

30. A compound according to claim 29, or a pharmaceutically acceptable salt thereof, wherein $R_c$ is H.

31. A compound according to claim 30, or a pharmaceutically acceptable salt thereof, wherein $R_a$ and $R_b$ are each independently selected from H and methyl.

32. A compound according to claim 31, or a pharmaceutically acceptable salt thereof, wherein $R_1$ is $C_{3-8}$ cycloalkyl-$C_{0-1}$ alkyl.

33. A compound according to claim 31, or a pharmaceutically acceptable salt thereof, wherein $R_1$ is $C_{4-6}$ alkyl.

34. A compound according to claim 33, or a pharmaceutically acceptable salt thereof, wherein $R_1$ is selected from isobutyl or 2,2-dimethylpropyl.

35. A compound according to claim 1, wherein the compound of formula (I) is selected from:
   2-Isobutyl-6-((3R)-3-(methylamino)pyrrolidin-1-yl)pyrimidin-4-amine;
   2-Isobutyl-6-(3-(methylamino)azetidin-1-yl)pyrimidin-4-amine;

2-(2,2-dimethylpropyl)-6-(3-(methylamino)azetidin-1-yl)
  pyrimidin-4-amine;
2-(2,2-dimethylpropyl)-6-((3R)-3-(methylamino)pyrrolidin-1-yl)pyrimidin-4-amine;
2-Cyclohexylmethyl-6-((3R)-3-(methylamino)pyrrolidin-1-yl)pyrimidin-4-amine;
2-Cyclohexylmethyl-6-(3-(methylamino)azetidin-1-yl)
  pyrimidin-4-amine;
2-(Cyclopropylmethyl)-6-(3-(methylamino)azetidin-1-yl)
  pyrimidin-4-amine; and
2-Cyclopropylmethyl-6-((3R)-3-(methylamino)pyrrolidin-1-yl)pyrimidin-4-amine;
and pharmaceutically acceptable salts thereof.

36. A pharmaceutical composition which comprises a compound of formula (I) according to claim 1, or a pharmaceutically acceptable salt thereof, and one or more pharmaceutically acceptable excipients.

37. A process for the preparation of a compound of formula (I), according to claim 1, comprising:

(a) reacting a compound of formula II

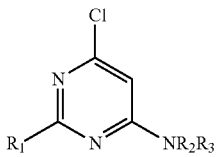

II with ammonia, benzophenoneimine, benzylamine or benzhydrylamine, wherein $R_1$, $R_2$ and $R_3$ have the same meaning as described in claim 1;

(b) reacting a compound of formula VII with a compound of formula IV

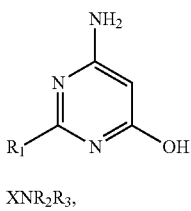

VII

IV wherein $R_1$, $R_2$ and $R_3$ have the same meaning described in claim 1 and X is H or tert-butoxycarbonyl, followed if necessary by the removal of any protecting group that may be present; or (c) reacting a compound of formula VIIB with a compound of formula IV

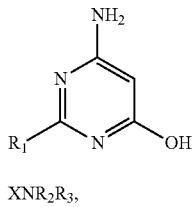

VII

IV wherein $R_8$ is halogen, triflate or tosylate, $R_1$, $R_2$ and $R_3$ have the same meaning described in claim 1, and X is H or tert-butoxycarbonyl, followed if necessary by the removal of any protecting group that may be present; or (d) when in a compound of formula (I), $R_1$ is $R_1'$—$CH_2$—$CH_2$—, treating a compound of formula IX with a source of hydrogen in the presence of a palladium catalyst

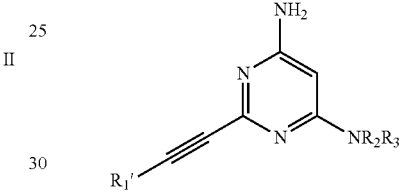

IX wherein $R_1'$ is selected from:
$C_{1-6}$ alkyl, $C_{3-6}$ cycloalkyl-$C_{0-4}$ alkyl, and aryl-$C_{0-4}$ alkyl, wherein any alkyl group may be optionally substituted by one or more halogen groups and the $C_{3-8}$ cycloalkyl group may be optionally substituted by one or more substituents independently selected from $C_{1-4}$ alkyl, halogen and aryl; or
$R_1'$ is a group of formula (i)

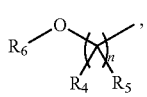

(i)

wherein n is 2 and $R_4$ and $R_5$ are each H; or
$R_1'$ is a group of formula (ii)

(ii)

wherein p is 2, $R_4$ and $R_5$ are each H, and $R_2$ and $R_3$ are as described in claim 1.

* * * * *

UNITED STATES PATENT AND TRADEMARK OFFICE
CERTIFICATE OF CORRECTION

PATENT NO. : 8,431,580 B2  
APPLICATION NO. : 12/809371  
DATED : April 30, 2013  
INVENTOR(S) : Elena Carceller González et al.

Page 1 of 1

It is certified that error appears in the above-identified patent and that said Letters Patent is hereby corrected as shown below:

In the Claims:

Claim 9, column 64, line 28: "$C_{3-6}$" should read --$C_{3-8}$--

Claim 10, column 64, line 36: "$C_{3-6}$" should read --$C_{3-8}$--

Claim 13, column 64, line 46: "$C_{1-6}$" should read --$C_{1-8}$--

Claim 37, column 68, line 34: "$C_{3-6}$" should read --$C_{3-8}$--

Signed and Sealed this  
Thirtieth Day of July, 2013

Teresa Stanek Rea  
*Acting Director of the United States Patent and Trademark Office*